US010414781B2

(12) United States Patent
Eddaoudi et al.

(10) Patent No.: US 10,414,781 B2
(45) Date of Patent: Sep. 17, 2019

(54) RARE EARTH-BASED METAL-ORGANIC FRAMEWORK FOR MOISTURE REMOVAL AND CONTROL IN CONFINED SPACES

(71) Applicant: King Abdullah University of Science and Technology, Thuwal (SA)

(72) Inventors: Mohamed Eddaoudi, Thuwal (SA); Rasha Abdulhalim, Thuwal (SA); Youssef Belmabkhout, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/766,413

(22) PCT Filed: Oct. 6, 2016

(86) PCT No.: PCT/IB2016/055999
§ 371 (c)(1),
(2) Date: Apr. 6, 2018

(87) PCT Pub. No.: WO2017/060856
PCT Pub. Date: Apr. 13, 2017

(65) Prior Publication Data
US 2018/0282350 A1    Oct. 4, 2018

Related U.S. Application Data

(60) Provisional application No. 62/237,985, filed on Oct. 6, 2015.

(51) Int. Cl.
| | |
|---|---|
| C07F 5/00 | (2006.01) |
| B01D 53/14 | (2006.01) |
| B01D 53/26 | (2006.01) |
| B01D 53/28 | (2006.01) |
| B01J 20/22 | (2006.01) |
| C02F 1/28 | (2006.01) |
| F25B 17/08 | (2006.01) |
| B01D 53/02 | (2006.01) |
| C02F 103/08 | (2006.01) |

(52) U.S. Cl.
CPC .............. *C07F 5/003* (2013.01); *B01D 53/02* (2013.01); *B01D 53/14* (2013.01); *B01D 53/261* (2013.01); *B01D 53/28* (2013.01); *B01J 20/226* (2013.01); *C02F 1/285* (2013.01); *F25B 17/08* (2013.01); *B01D 2253/204* (2013.01); *B01D 2253/306* (2013.01); *B01D 2253/31* (2013.01); *B01D 2253/311* (2013.01); *B01D 2255/206* (2013.01); *B01D 2255/2061* (2013.01); *B01D 2255/2063* (2013.01); *B01D 2255/2065* (2013.01); *B01D 2255/2066* (2013.01); *B01D 2255/2068* (2013.01); *B01D 2257/80* (2013.01); *B01D 2258/06* (2013.01); *B01D 2259/4508* (2013.01); *B01D 2259/4566* (2013.01); *B01D 2259/4575* (2013.01); *C02F 2103/08* (2013.01)

(58) Field of Classification Search
None
See application file for complete search history.

(56) References Cited

FOREIGN PATENT DOCUMENTS

| | | | |
|---|---|---|---|
| WO | 2014033481 A2 | 3/2014 | |
| WO | WO-2014033481 A2 * | 3/2014 | ............... C07C 7/12 |

OTHER PUBLICATIONS

Furukawa et al., J Am. Chem. Soc. 2014, 136, 4369-4381. (Year: 2014).*
Warren et al., Angew. Chem. Int. Ed. 2014, 53, 4592-4596, (Supporting Materials) (Year: 2014).*
Warren et al., Angew. Chem. Int. Ed. 2014, 53, 4592-4596. (Year: 2014).*
Warren NPL 2014—Supporting Material (Year: 2014).*
Alezi, et al., "Quest for Highly Connected Metal-Organic Framework Platforms: Rare-Earth Polynuclear Clusters Versatility Meets Net Topology Needs", Journal of the American Chemical Society, 2015, 137, 5421-5430.
Arundel, et al., "Indirect Health Effects of Relative Humidity in Indoor Environments", Environmental Health Perspectives vol. 65, pp. 351-361, 1986.
Assen, et al., "Ultra-Tuning of the Rare-Earth fcu-MOF Aperture Size for Selective Molecular Exclusion of Branched Paraffins", Angew. Chem. Int. Ed. 2015, 54, 14533-14358.
Feng, et al., "A Highly Stable Porphyrinic Zirconium Metal-Organic Framework with shp-a Topology", J. Am. Chem. Soc. 2014, 136, 17714-17717.
Ferey, et al., "A Chromium Terephthalate-Based Solid with Unusually Large Pore Volumes and Surface Area", Science, vol. 309, Sep. 23, 2005, pp. 2040-2042.
Furukawa, et al., "Water Adsorption in Porous Metal-Organic Frameworks and Related Materials", J. Am. Chem. Soc. 2014, 136, 4369-4381.

(Continued)

*Primary Examiner* — Clinton A Brooks
*Assistant Examiner* — Kofi Adzamli
(74) *Attorney, Agent, or Firm* — Billion & Armitage; Lisbeth C. Robinson

(57) ABSTRACT

A method for preparing a metal-organic framework (MOF) comprising contacting one or more of a rare earth metal ion component with one or more of a tetratopic ligand component, sufficient to form a rare earth-based MOF for controlling moisture in an environment. A method of moisture control in an environment comprising adsorbing and/or desorbing water vapor in an environment using a MOF, the MOF including one or more of a rare earth metal ion component and one or more of a tetratopic ligand component. A method of controlling moisture in an environment comprising sensing the relative humidity in the environment comprising a MOF; and adsorbing water vapor on the MOF if the relative humidity is above a first level, sufficient to control moisture in an environment. The examples relate to a MOF created from 1,2,4,5-Tetrakis(4-carboxyphenyl)benzene (BTEB) as tetratopic ligand, 2-fluorobenzoic acid and Y(NO3)3, Tb(NO3)3 and Yb(NO3)3 as rare earth metals.

11 Claims, 26 Drawing Sheets

(56) References Cited

OTHER PUBLICATIONS

Furukawa, et al., "Water Adsorption in Porous Metal-Organic Frameworks and Related Materials", Journal of the American Chemical Society, Mar. 3, 2014, 4369-4381.
Grinshpun, et al., "Control of Aerosol Contaminants in Indoor Air: Combining the Particle Concentration Reduction with Microbial Inactivation", Environ. Sci. Technol. 2007, 41, 606-612.
Guillerm, et al., "A supermolecular building approach for the design and construction of metal-organic frameworks", Chem. Soc. Rev., 2014, 43, 6141-6172.
Guillerm, et al., "Discovery and introduction of a (3,18)- connected net as an ideal blueprint for he design of metal-organic frameworks", Nature Chemistry, vol. 6, Aug. 2014, pp. 673-680.
Guo, et al., "Microporous Coordination Polymers as Efficient Sorbents for Air Dehumidification", Langmuir 2014, 30, 1921-1925.
Jeremias, et al., "MIL-100(Al, Fe) as water adsorbents for heat transformation purposes—a promising application", J. Meter. Chem., 2012, 22, 10148-10151.
Khutia, et al., "Water Sorption Cycle Measurements on Functionalized MIL-101Cr for Heat Transformation Application", Chem. Mater. 2013, 25, 790-798.
Luebke, et al., "Versatile rare earth hexanuclear clusters for the design and synthesis of highly-connected ftw-MOFs", Chem. Sci., 2015, 6, 4095-4102.
Nagda, et al., "Low Relative Humidity and Aircraft Cabin Air Quiality", Indoor Air 2001; 11: 200-214.
Salles, et al., "Molecular Insight into the Adsorption and Diffusion of Water in the Versatile Hydrophilic/Hydrophobic Flexible MIL-53(Cr) MOF", The Journal of Physical Chemistry, 2011, 115, 10764-10776.
Seo, et al., "Energy-Efficient Dehumidification over Hierachically Porous Metal-Organic Frameworks as Advanced Water Adsorbents", Advanced Materials, 2012, 24, 806-810.
Xue, et al., "Tunable Rare-Earth fcu-MOFs: A Platform for Systematic Enhancement of $CO_2$ Adsorption Energetics and Uptake", J. Am. Chem. Soc. 2013, 135, 7660-7667.
Notification of Transmittal of the International Search Report and the Written Opinion of the International Searching Authority, or the Declaration for PCT/IB2016/055999 dated Mar. 2, 2017.
Warren, et al., "Shape Selectivity by guest-Driven Restructuring of a Porous Material", Angew.Chem.Int. Ed, 53, 2014, 4592-4596.

* cited by examiner

Hexagonal P
63/mmc
a= b =22.0036
c = 24.6711

Density: 0.92 g cc$^{-1}$
%FV : 61.39%
PV : 0.66 cc g$^{-1}$

RARE EARTH-BASED METAL-ORGANIC FRAMEWORK FOR MOISTURE REMOVAL AND CONTROL IN CONFINED SPACES

This application is a National Stage Application of PCT/IB2016/055999, filed on Oct. 6, 2016, which claims benefit of Application No. 62/237,985, filed on Oct. 6, 2015 in the United States of America and which applications are incorporated herein by reference. A claim of priority to all, to the extent appropriate, is made.

BACKGROUND

Today, conventional vapor compression air conditioning systems are the most common methods of controlling humidity in an environment. Such systems generally pass a humid air stream over a cooler where water vapor condenses out of the humid air before it exits the system in a liquid phase. In most instances, the condensation of water vapor from humid air is driven by a temperature gradient. These systems typically use pumps, fans, and other similar devices to deliver the humid air stream to the system, remove the condensed water vapor from the system, and recirculate the less humid air back into the environment. As a consequence of these features, these systems consume large amounts of energy.

The challenge of controlling moisture levels is particularly difficult in a confined environment, such as airplanes, space shuttles, and submarines, where there is limited to no circulation of air, large volumes of air to dehumidify, and energy consumption is high and costly. Conventional systems also present challenging issues relating to design capacity. As the amount of humidity to be removed from an environment increases, the size of the system must increase. This increase in size results in a corresponding increase in costs. Another challenge is maintaining moisture levels in environments with high humidity within the American Society of Heating, Refrigerating, and Air-Conditioning Engineers' recommended range of 45% relative humidity (or even lower) to 65% relative humidity.

SUMMARY OF THE INVENTION

In general, this disclosure describes embodiments relating to rare earth-based metal-organic frameworks with shp topology. More specifically, this disclosure describes a rare earth-based metal-organic framework with shp topology that, among other things, exhibits outstanding properties with respect to moisture removal and control.

This disclosure describes embodiments that include a method of preparing a rare earth-based metal-organic framework with shp topology by contacting one or more of a rare earth metal ion component with one or more of a tetratopic ligand component.

This disclosure also describes embodiments that include a metal-organic framework composition comprising one or more of a rare earth metal ion component and one or more of a tetratopic ligand component, wherein one or more of the rare earth metal ion component and one or more of the tetratopic ligand component associate to form a shp topology.

This disclosure further describes embodiments that include a method of controlling the amount of moisture in an environment, comprising sensing the relative humidity in the environment using a metal-organic framework, adsorbing water vapor if the relative humidity is above a first level, and releasing water vapor if the relative humidity is below a second level.

This disclosure describes embodiments that include a method of using a metal-organic framework, comprising desalinating a water using a short pressure gradient swing adsorption, wherein a rare earth-based metal-organic framework with shp topology is used as an adsorbent. This disclosure also describes embodiments that include a method of using a metal-organic framework, comprising heating and/or cooling a pump, wherein the heating and/or cooling of the pump is by the adsorption-desorption of water vapor on a rare earth-based metal-organic framework with shp topology. The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

Figure 1:
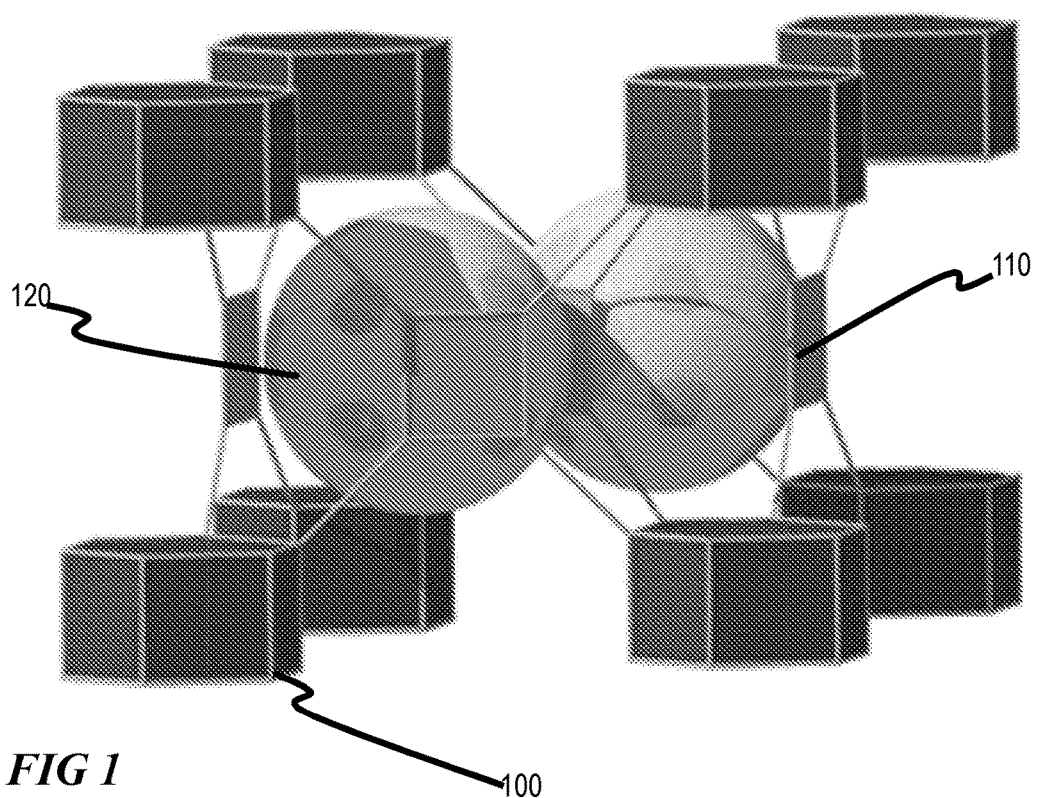
FIG. 1 illustrates a schematic representation of a rare earth-based metal-organic framework with shp topology, according to some embodiments.

The present invention relates to a microporous metal-organic framework (MOF), including one or more rare earth metals. The disclosure herein provides compositions, methods of preparing, and methods of using a rare earth-based shp-MOF. The rare earth-based shp-MOF disclosed herein exhibits outstanding properties with respect to moisture removal and control. The rare earth-based shp-MOF disclosed herein exhibits high stability for water vapor, and a high uptake and affinity for water vapor at high humidity. Embodiments provided herein describe a rare earth-based shp-MOF that controls moisture levels in a confined environment with limited or no air circulation with a thermodynamic maximum working capacity of about 0.45 g/g. Embodiments describe the adsorption and desorption of water vapor on and from a rare earth-based shp-MOF to control moisture levels in an environment, wherein the adsorption-desorption is driven by a moisture gradient. Embodiments provided herein describe a method of maintaining moisture levels in a range of relative humidity recommended by health and safety in confined spaces and work spaces. Embodiments also describe a method of bulk removal of moisture from an environment with high humidity. A rare earth-based MOF with shp topology is a newly discovered microporous MOF material that can be used in an autonomous moisture controlled swing adsorption system to control moisture levels in confined spaces such as space shuttles and aircraft cabins. Numerous other advantages and uses of a rare earth-based shp-MOF will be readily apparent to one of skill in the art. Although embodiments of the present disclosure generally include a metal-organic framework with shp topology, any topology may be utilized to carry out the present invention.

The figures referenced in the description of the many embodiments of this disclosure are not necessarily drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Many terms used herein are defined below. Other terms not expressly defined should be read in the context of this specification before being given their ordinary meanings as understood by one of skill in the art.

As used herein, "confined environment" or "confined space" refers to an area with limited to no circulation of air.

As used herein, "relative humidity" or "RH" refers to the ratio of the actual partial pressure of water vapor to the equilibrium or saturated vapor pressure of water at a given temperature.

As used herein, "rare earth metal ion component" and "rare earth-based" refers to one or more of a rare earth element, including cerium, dysprosium, erbium, europium, gadolinium, holmium, lanthanum, lutetium, neodymium, praseodymium, promethium, samarium, scandium, terbium, thulium, ytterbium, yttrium, and combinations thereof.

As used herein, "DMA" refers to a dimethylammonium cation.

As used herein, "solv" refers to a solvent.

As used herein, "RE" refers to rare earth.

Owing to the inventions of the contemporary age, our lifestyle has morphed from previously open-air residential and occupational environments into more enclosed air-conditioned ones, particularly in regions with extreme hot and cold weather. One of the most critical challenges facing engineers in indoor environments, more so in confined spaces, is regulating the escalating levels of humidity levels. The appropriate indoor relative humidity (RH) levels for a healthy and comfortable atmosphere for occupied structures lies between 45% RH and 65% RH, as recommended by the American Society of Heating, Refrigerating, and Air-Conditioning Engineers (ASHRAE).

Of particular concern are cases of confined spaces where the humidity level needs to be maintained with limited or no access to fresh air, such as space shuttles, airplane cabins, submarines, etc. For example, moisture-control problems are evident in residential buildings, museums, schools, office spaces, and shopping malls, as well as in other confined spaces with the excessive amount of moisture released by human activities. An increase in RH leads to condensation on windows and walls, as well as a physical sensation of dampness as the warm, moisture-loaded air comes into contact with a colder surface. One of the main concerns upon moisture accumulation, in the absence of proper control measures such as ventilation and sorbents, is the growth of mold, mildew and other fungi. Recent studies have shown that prolonged exposure to toxigenic fungi is directly related to high levels of allergies, and infectious diseases.

With respect to confined spaces, control of moisture levels must sometimes be maintained without fresh air introduction which imposes additional ventilation challenges. Therefore, maintaining relative humidity levels between 45% RH and 65% RH may be crucial to provide a comfortable environment, as well as prevent various respiratory and central nervous system problems attributed to fungal growth. During airplane flights, the average relative humidity level ranges at elevated altitudes drops considerably ranging from 14% RH to 19% RH, where temperatures often drop and the air becomes thin, losing its ability to hold much water. The chief sources of moisture on-board are limited to the evaporation of water from passengers' hygienic activities, perspiration and respiration, exposed food and drinks and water spills. Although active humidification systems can be installed to adjust humidity levels, the current systems impose weight constraints on the airplane and condensation hazards, which might cause corrosion and electrical faults.

With respect to high relative humidity levels (exceeding 65% RH), dehumidification is often achieved either by conventional vapor compression air conditioning systems or by desiccants (such as zeolites, active carbon and silica gels). Vapor compression systems require the installation of bulky and expensive machinery, which demands energy intensive operating systems, imposing weight and space constraints on the aircraft. On the other hand, desiccants are porous materials that have high affinity for water, which can be regenerated utilizing heat from energy sources such as electricity or solar energy; therefore, desiccants would be more favorable since they are generally light and easy to handle. However, it is essential to point out that commercial desiccants only act as dehumidifiers.

Therefore, in order to regulate humidity levels in the cabin for a safe and comfortable environment as recommended by ASHREA, an ideal adsorbent material should swiftly adsorb water vapor as humidity levels reach 65% RH and desorb water vapor as humidity levels drop below 45% RH. Such a material, if available, will pave the way towards alleviating the various existing burdens using conventional techniques pertaining to the design capacity, energy-efficiency and the overall cost.

A MOF is a crystalline material that combines ligands and metal ions or metal clusters to form one-, two-, and three-dimensional networked structures with large surface areas that can be porous. MOFs are a unique class of hybrid porous materials that exhibit, among other things, exceptional porosity, chemical stability, and modularity. The molecular building block approach (MBB) is used to design application-specific and high performance MOFs. It is the assembly of highly connected and edge-transitive nets that limits the number of possible topological outcomes, leading to structures with highly symmetric topologies. Using the MBB, a rare earth-based MOF with shp topology is obtained.

The present disclosure relates to a Y-shp-MOF-5 as a unique energy-efficient adsorbent with dual humidifying/dehumidifying operations in the optimal range 45%-65% RH with an equilibrium water uptake and working capacity of 50 wt % and 35 wt %, respectively. The observed s-shaped water adsorption isotherm at room temperatures (RT), with adsorption and desorption branches concentrated at relative humidies higher and lower than 50% RH, respectively, was particularly beneficial in an autonomous moisture controlled swing adsorption approach, regulated only by the changes in the relative humidity between 25% and 85% RH (8 and 26 mbar) at room temperature. The equilibrium uptake was determined at a specific relative humidity (water vapor pressure), while the working capacity was derived from the difference in the water equilibrium uptake between two relative humidity levels. The capturing of moisture at relative humidity higher than 50% RH and the subsequent release of moisture from Y-shp-MOF-5 below 50% RH were uniquely very high and equal and lies matchlessly within the ASHREA recommendations for a comfortable environment in enclosed spaces.

The unique adsorption properties of Y-shp-MOF-5 were studied by a combination of water adsorption and in-situ single crystal X-ray studies. Systematic in situ single crystal diffraction studies carried out under different humidity conditions allowed us to localize the adsorbed water molecules and to gain a better understanding on the water-framework interactions governing the unique water adsorption properties of the shp-MOF-5. The inimitable performance of shp-MOF-5 for moisture control was delineated by comparing it performances with the best solid state materials, with and without S-shaped water adsorption uptake, including MOFs, Zeolites, Clay and Mesoporous Silica.

The present invention relates to a highly connected and highly stable rare earth-based metal-organic framework with shp topology that exhibits, among other things, outstanding properties with respect to moisture control and removal.

Figure 2A:
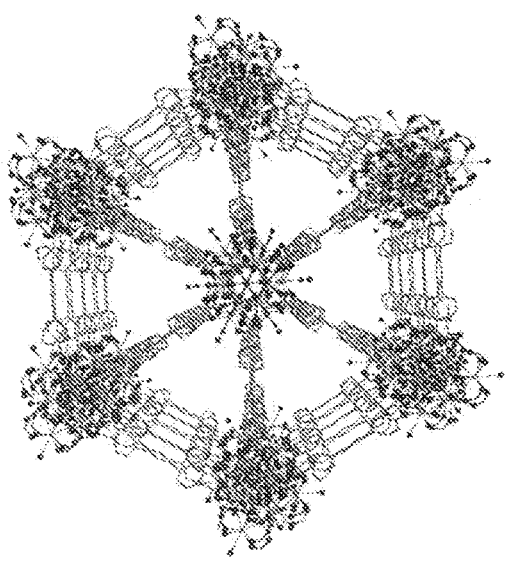
FIG. 2A illustrates a schematic representation of a rare-earth based MOF with shp topology shown as a material that crystallizes in the hexagonal space group P63/mmc, according to some embodiments.
Figure 2B:
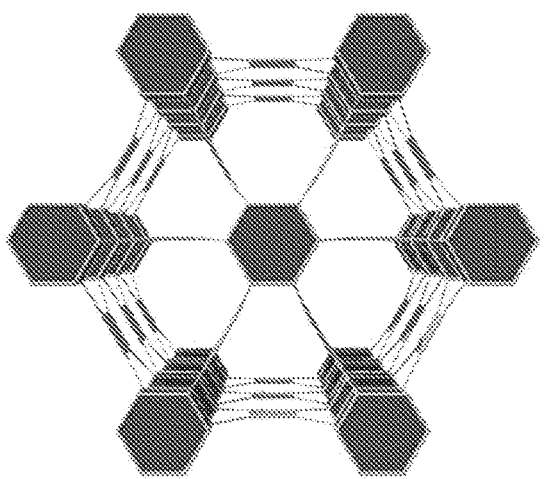
FIG. 2B illustrates a schematic representation of a rare-earth based MOF with shp topology with its theoretical density and pore volume provided as 0.92 g·cm$^{-3}$ and 0.66 cm$^3$·g$^{-1}$, respectively, according to some embodiments.
Figure 3A:
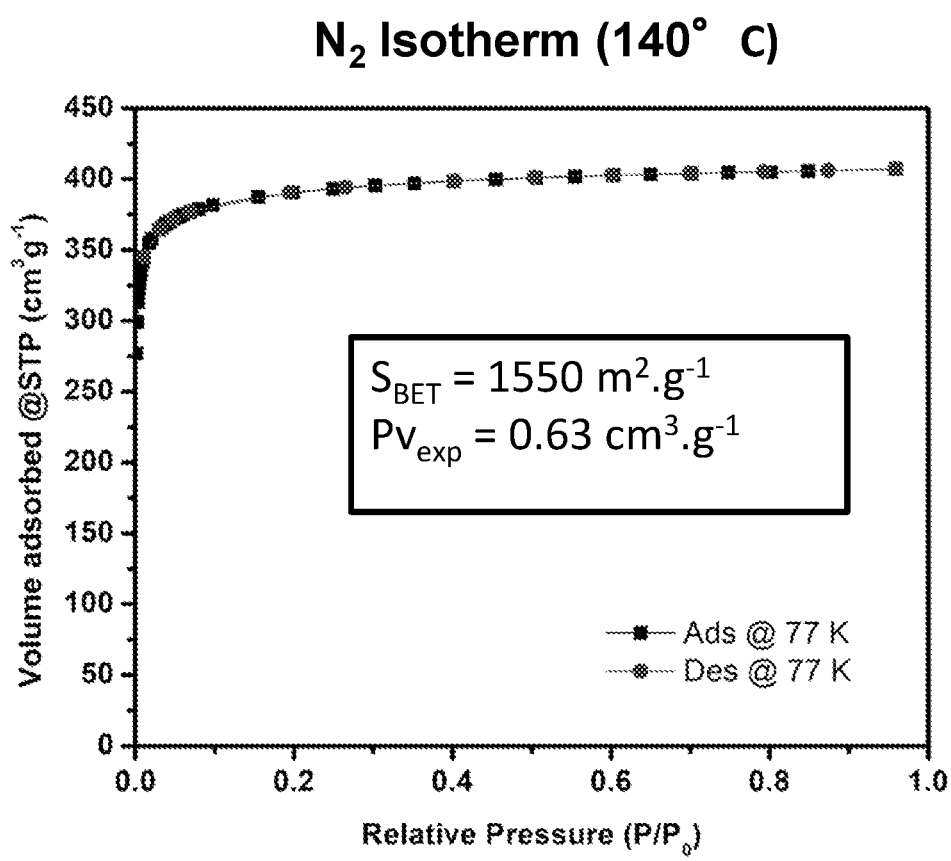
FIG. 3A illustrates a graphical view of $N_2$ sorption isotherms for a rare-earth based metal-organic framework with shp topology at 77K indicating the volume adsorbed at various pressures, according to some embodiments.
Figure 3B:
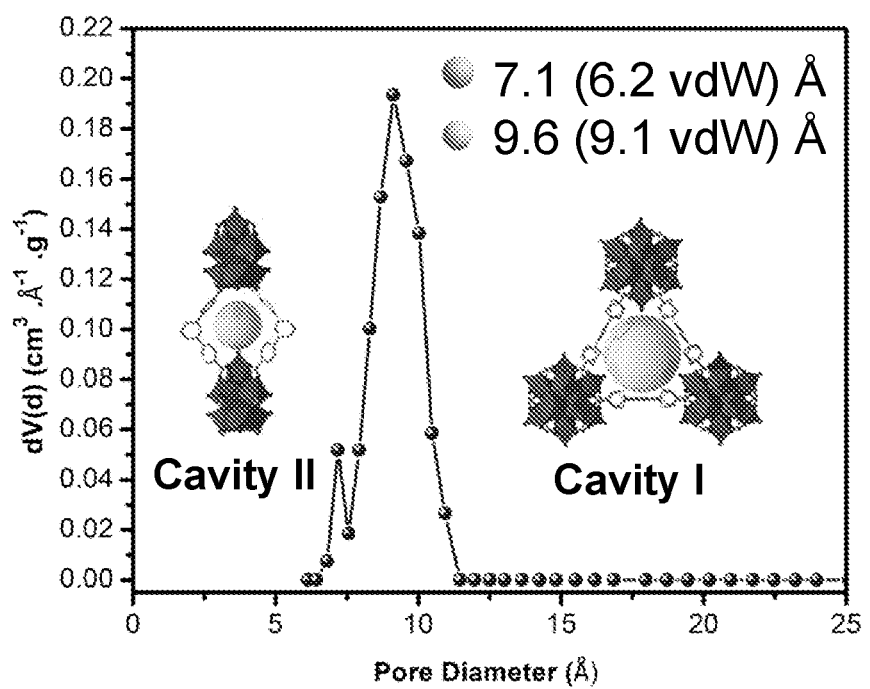
FIG. 3B illustrates a graphical view of the pore size distribution in a rare-earth based metal-organic framework with shp topology and a schematic representation of a Cavity I and a Cavity II, according to some embodiments.

The composition of a rare earth-based MOF with shp topology includes one or more metal ions 100 in contact with one or more tetratopic ligands 110 sufficient to form an shp topology as shown in FIG. 1. In some embodiments, a shp topology of a rare earth-based MOF is described as a material that crystallizes in the hexagonal space group P63/mmc, as shown in FIG. 2A, with a theoretical density and pore volume of 0.92 g·cm$^{-3}$ and 0.66 cm$^3$·g$^{-1}$ respectively, as shown in FIG. 2B. As shown in FIG. 3A, the experimental BET specific surface area and pore volume are 1550 m$^2$·g$^{-1}$ and 0.63 cm$^3$·g$^{-1}$, respectively. FIG. 3A further illustrates the N$_2$ adsorption at 77 K. FIG. 3B illustrates the pore size distribution.

Figure 4:
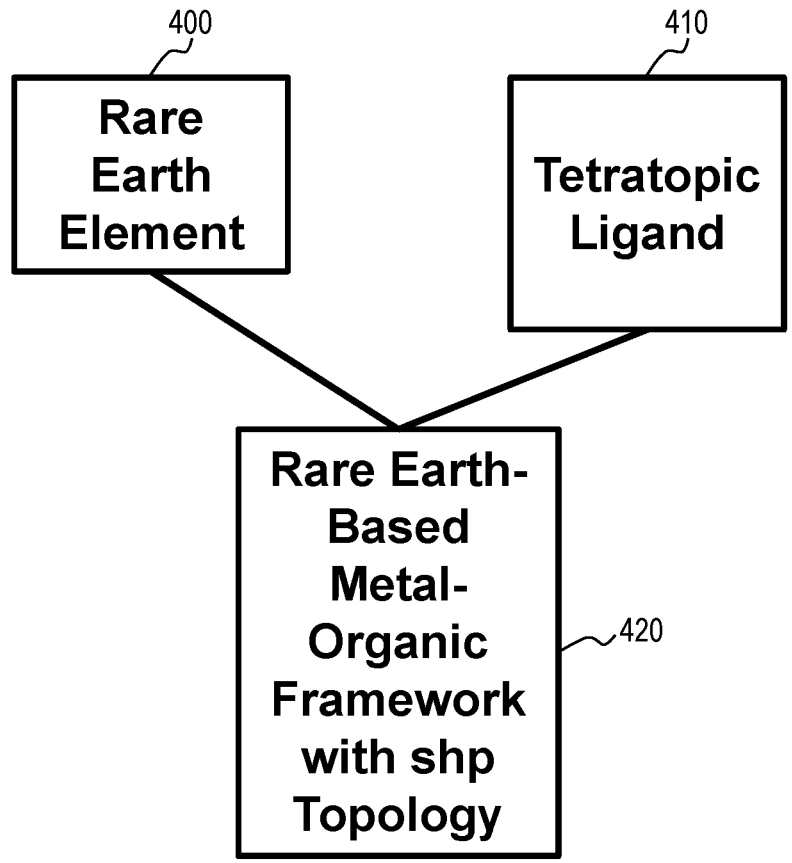
FIG. 4 is a block flow diagram that illustrates the components that react to form a metal-organic framework comprised of one or more of a rare earth metal ion component with one or more of a tetratopic ligand component that associate to form a shp topology, according to some embodiments.

FIG. 4 illustrates a method of preparing a rare earth-based MOF with shp topology, wherein one or more rare earth metal ions components 400 react with one or more tetratopic ligand components 410 to produce a rare earth-based MOF with shp topology 420.

A rare earth-based MOF with shp topology can be comprised of a variety of rare earth metal ion components 400. In some embodiments, the rare earth metal ion component is one or more of yttrium ions. In some embodiments, the rare earth metal ion component is one or more of the following rare earth elements: cerium, dysprosium, erbium, europium, gadolinium, holmium, lanthanum, lutetium, neodymium, praseodymium, promethium, samarium, scandium, terbium, thulium, ytterbium, or yttrium. In some embodiments, the rare earth metal ion component is characterized by the formula RE(NO$_3$)$_3$.xH$_2$O.

A rare earth-based MOF with shp topology can be coordinated with a tetratopic ligand 410. The tetratopic ligand can be rectangular or quadrangular shaped. The tetratopic ligand can act as a molecular building block. The tetratopic ligand can be a rectangular/quadrangular molecular building block. In some embodiments, a modulator is used for the in situ formation of highly connected polynuclear carboxylate-based clusters. In some embodiments, a 12-connected rare earth molecular building block is formed in situ by the addition of an excess amount of a modulator, such as 2-fluorobenozic acid (2-FBA). According to some embodiments, the tetratopic ligand is rectangular-shaped 1,2,4,5-tetrakis(4-carboxyphenyl)benzene (BTEB).

Figure 5:
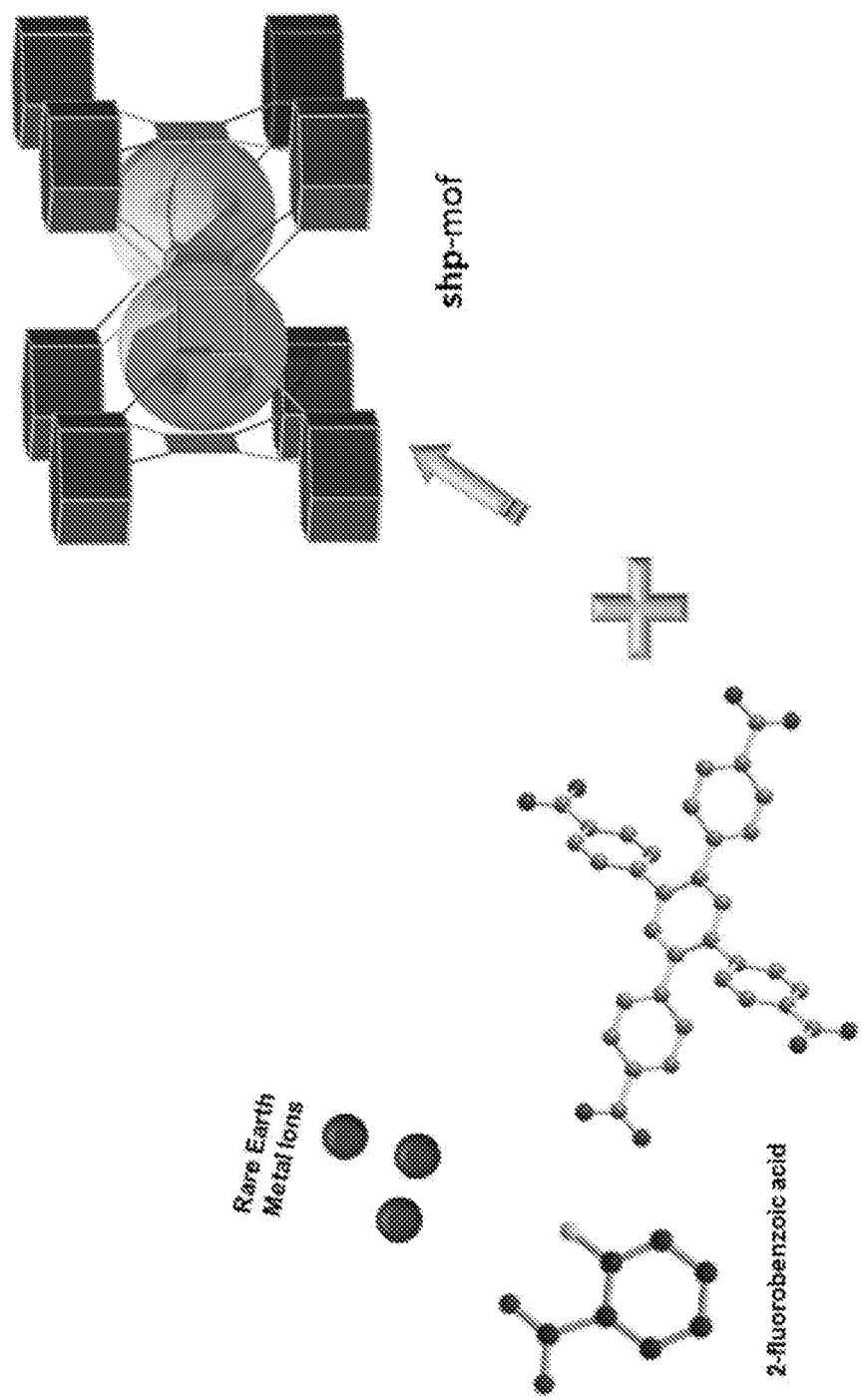
FIG. 5 illustrates a schematic reaction of 4-c, 1,2,4,5-Tetrakis (4-carboxyphenyl)benzene with Y(NO$_3$). 6H$_2$O in the presence of 2-fluorobenzoic acid that produces a rare earth-based metal-organic framework with shp topology, according to some embodiments.

To prepare a rare earth-based MOF with shp topology, a rare earth metal ion component is contacted with a tetratopic ligand component in a solution mixture of dimethyl formamide (DMF), fluorobenzoic acid, and water. In some embodiments, as shown in FIG. 5, a rare earth-based MOF with shp topology is prepared by reacting an amount of 4-c, 1,2,4,5-Tetrakis (4-carboxyphenyl)benzene (BTEB) with an amount of Y(NO$_3$)$_3$.6H$_2$O in the presence of an amount of 2-fluorobenzoic acid.

Figure 6A:
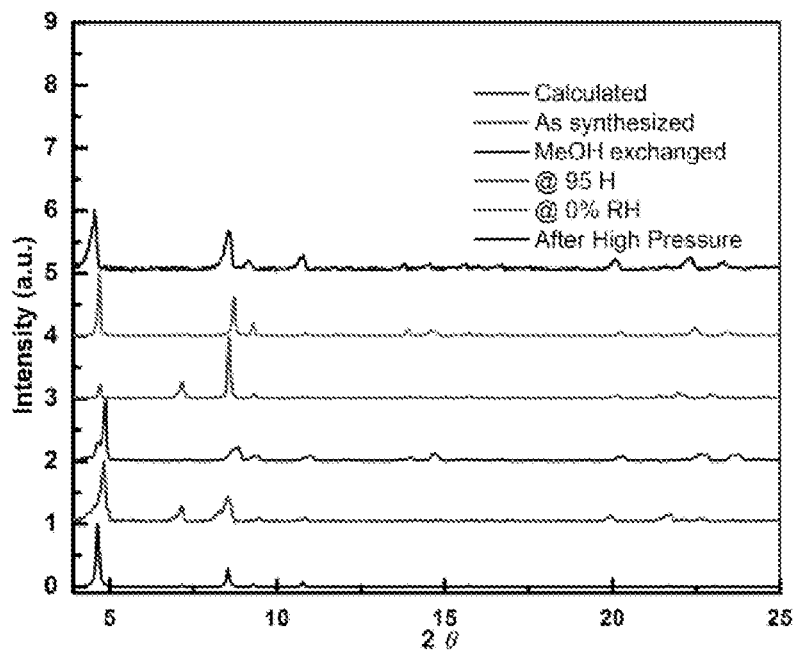
FIG. 6A illustrates a graphical view of experimental and calculated powder X-ray diffraction patterns indicating the stability of a rare earth-based metal-organic framework with shp topology at different amounts of relative humidity, according to some embodiments.
Figure 6B:
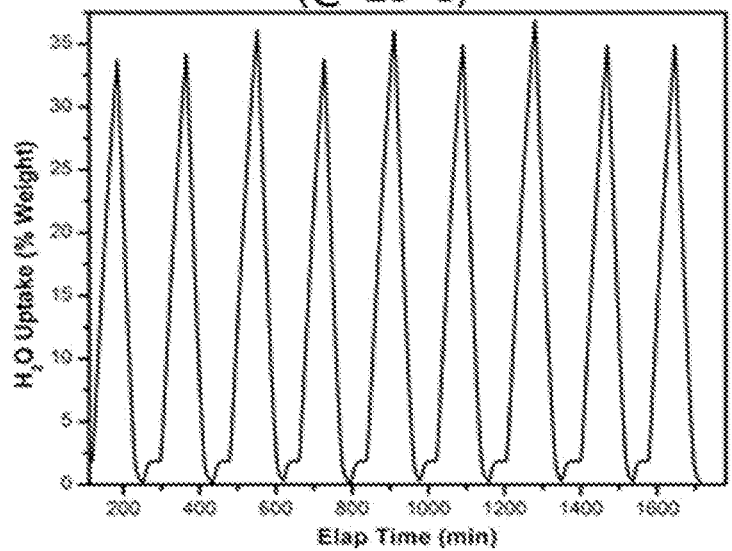
FIG. 6B illustrates a graphical view of cyclic adsorption-desorption measurements of water vapor on a rare earth-based metal-organic framework with shp topology at 25° C. in response to relative humidity changes of 0% relative humidity, 25% relative humidity, and 80% relative humidity, according to some embodiments.

A rare earth-based MOF with shp topology exhibits high stability for water vapor and hydrogen sulfide. As shown in FIG. 6A, experimental and calculated powder X-ray diffraction patterns of shp-MOF at different conditions confirmed shp-MOF's high stability for water vapor at various amounts of relative humidity. As shown in FIG. 6B, shp-MOF's high stability for water vapor was also confirmed by cyclic adsorption-desorption measurements at various relative humidity, including about 0% relative humidity, about 25% relative humidity, and about 80% relative humidity.

In some embodiments, an adsorption isotherm for a rare earth-based MOF with shp topology exhibits low H$_2$O uptake at low to moderate relative humidity. In some embodiments, this first uptake of H$_2$O occupies open metal sites. As relative humidity increases, a sharp increase in H$_2$O uptake is observed. After this sharp increase, the adsorption isotherm exhibits a high H$_2$O uptake and high affinity for water vapor at high relative humidity. A rare earth-based shp-MOF also exhibits desorption. As relative humidity decreases, a sharp decrease in H$_2$O uptake is observed before H$_2$O uptake remains low. In some embodiments, the adsorption-desorption of H$_2$O is driven by a moisture gradient, resulting in an energy-efficient process. These unique adsorption-desorption properties of a rare earth-based shp-MOF exhibit optimal characteristics for moisture control in a confined environment.

Figure 7:
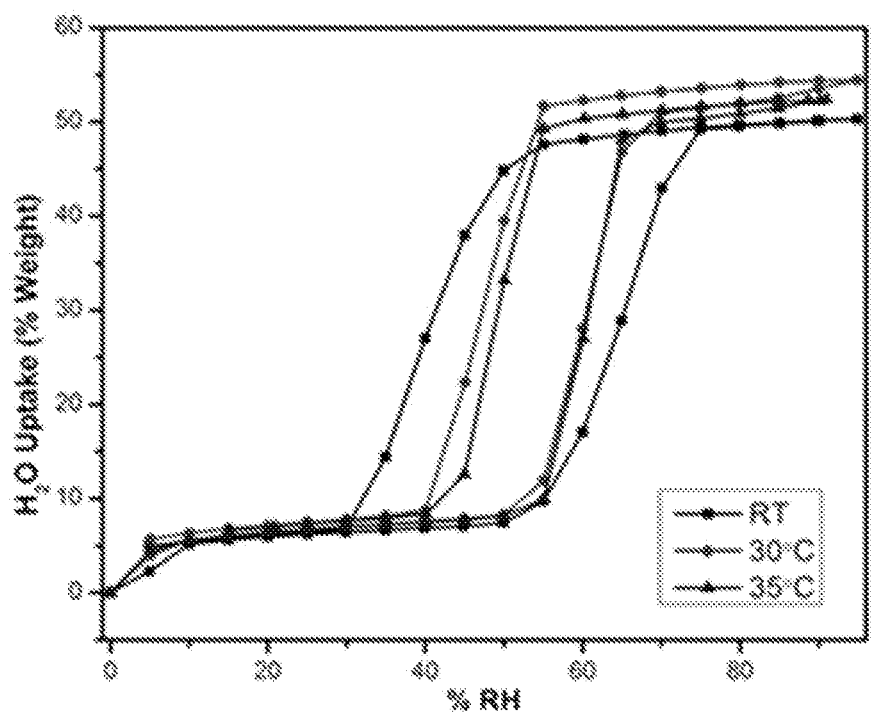
FIG. 7 illustrates a graphical view of H$_2$O sorption isotherms for a rare earth-based metal-organic framework with shp topology at various temperatures indicating H₂O uptake at various amounts of relative humidity, according to some embodiments.

FIG. 7 illustrates a water sorption isotherm for a rare earth-based shp-MOF at room temperature, 30° C., and 35° C. On the vertical axis is $H_2O$ uptake by weight percentage, with percent relative humidity on the horizontal axis. In some embodiments, as shown by FIG. 5, at room temperature, $H_2O$ uptake is 5 wt % between a range of 10% relative humidity and 55% relative humidity. As relative humidity increases from 55% to 70%, $H_2O$ uptake sharply increases to 50 wt %. As relative humidity decreases from 45% to 30%, $H_2O$ uptake sharply decreases from 50 wt % to 5 wt %. In some embodiments, a rare earth-based shp-MOF at room temperature reduces relative humidity to 30% in a process driven by a moisture gradient. In some embodiments, a rare earth-based shp-MOF exhibits high $H_2O$ uptake at 70% relative humidity.

In some embodiments, as shown by FIG. 7, at 30° C., $H_2O$ uptake is 5 wt % between a range of 10% relative humidity and 50% relative humidity. As relative humidity increases from 50% to 65%, $H_2O$ uptake sharply increases to 50 wt %. As relative humidity decreases from 55% to 40%, $H_2O$ uptake sharply decreases from 50 wt % to 5 wt %.

In some embodiments, as shown by FIG. 7, at 35° C., $H_2O$ uptake is 5 wt % between a range of 10% relative humidity and 50% relative humidity. As relative humidity increases from 50% to 65%, $H_2O$ uptake sharply increases to 50 wt %. As relative humidity decreases from 55% to 40%, $H_2O$ uptake sharply decreases from 50 wt % to 5 wt %.

The shape of the water adsorption isotherm render the rare earth-based MOF with shp topology a suitable material for adsorption desalination using short pressure gradient swing adsorption. Further, the exothermic and endothermic effects during adsorption and desorption of water, respectively, and the swing adsorption driven by the reduction of relative humidity from about 30% and 80% RH, can be used to heat and/or cool one or more of a pump.

Figure 8:
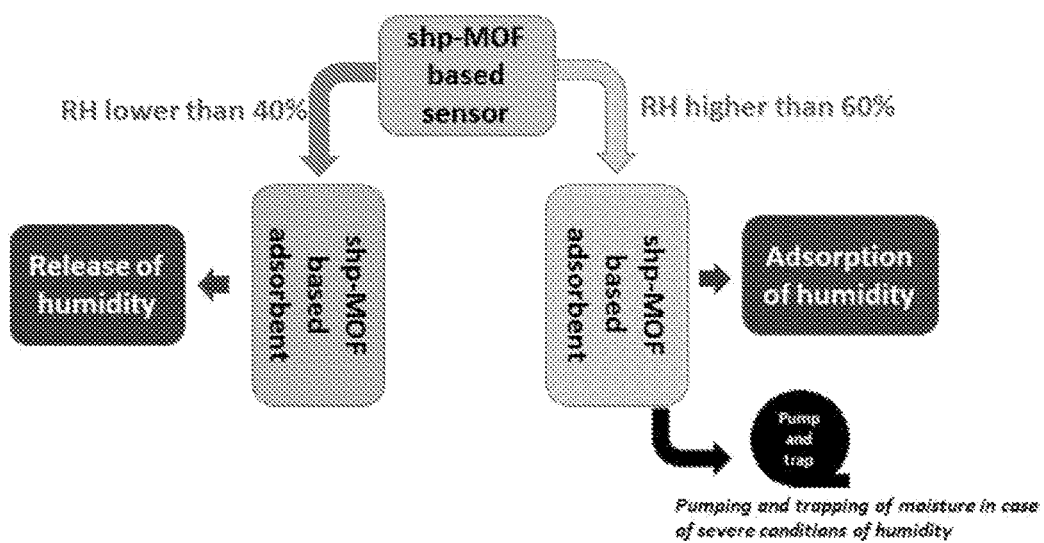
FIG. 8 illustrates a flow diagram of a method for controlling the relative humidity in an environment using a rare earth-based metal-organic framework with shp topology, according to some embodiments.

In some embodiments, a rare earth-based shp-MOF operates as a system capable of maintaining relative humidity between a desired range of relative humidity in a confined environment. In some embodiments, as shown in FIG. 8, the system comprises a sensor, humidifier, and dehumidifier wherein the sensor detects moisture levels lower than about 40% relative humidity and greater than about 60% relative humidity. If the moisture level is lower than about 40% relative humidity, the system's humidifier releases humidity until the relative humidity increases above about 40%. If the moisture level is greater than about 60% relative humidity, the system's dehumidifier adsorbs humidity until the relative humidity decreases below about 60%.

In some embodiments, the system operates at moisture levels between about 30% relative humidity and about 70% relative humidity. In some embodiments, the system captures and releases water vapor. In other embodiments, the system only captures water vapor. In other embodiments, the system only releases water vapor. In other embodiments, the system comprises a sensor that also captures and releases water vapor. Numerous other arrangements and operating ranges of relative humidity are possible as will be readily apparent to one of skill in the art.

EXAMPLE

Rare Earth-Shp-MOF-5

Starting materials included, for example, 1,2,4,5-tetrakis (4-carboxyphenyl)benzene (BTEB), 2-fluorobenzoic acid (2-FBA), N,N-Dimethylformamide (DMF); anhydrous acetone was obtained from Acros Organics. All chemicals and solvents were used as received without further purification from Fisher Scientific, Acros Organics, Sigma-Aldrich, or TCI America.

Preparation of $[Y_9L_{12}(H_2O)_n]_n$(Y-shp-MOF-5): To a 20 mL glass scintillation vial containing BTEB (6.7 mg, 0.012 mmol) dissolved in 0.5 ml DMF, a 0.5 ml 0.068 M Y $(NO_3)_3 \cdot 6H_2O$ in DMF (0.034 mmol). To this 2.01 mL 4M 2-fluorobenzoic acid (8.04 mmol) in DMF and 0.75 ml $H_2O$ were added. The vial was sealed and placed into a preheated oven at 105° C. for 24 h. Colorless hexagonal bipyramidal crystals were obtained.

Preparation of $[Tb_9L_{12}(H_2O)_n]_n$(Tb-shp-MOF-5). To a 20 mL glass scintillation vial containing BTEB (6.7 mg, 0.012 mmol) dissolved in 0.5 ml DMF, a 0.5 ml 0.068M Tb $(NO_3)_3 \cdot 5H_2O$ in DMF (0.034 mmol). To this 2.01 mL 4M 2-fluorobenzoic acid (8.04 mmol) in DMF and 0.25 ml $H_2O$ was added. The vial was sealed and placed into a preheated oven at 105° C. for 48 h. Colorless hexagonal bipyramidal crystals were obtained.

Preparation of $[Yb_9L_{12}(H_2O)_n]_n$(Yb-shp-MOF-5). To a 20 ml glass scintillation vial containing BTEB (6.7 mg, 0.012 mmol) dissolved in 0.5 ml DMF, a 0.5 ml 0.068M Yb$(NO_3)_3 \cdot 6H_2O$ in DMF (0.034 mmol). To this 2.01 mL 4M 2-fluorobenzoic acid (8.04 mmol) in DMF, 0.75 ml $H_2O$ and 0.1 ml $HNO_3$ (3.5M) was added. The vial was sealed and placed into a preheated oven at 105° C. for 48 h. Colorless hexagonal bipyramidal crystals were obtained.

Materials and Methods (Instrumentation). Data from single-crystal X-ray diffraction (SCXRD) studies were collected on two different instruments. (1) An X8 PROSPECTOR APEX II CCD diffractometer (Cu Kα λ=1.54178 Å) and (2) Bruker Apex II DUO CCD diffractometer with a multilayer monochromator (Mo Kα λ=0.71073 Å).

Powder X-ray diffraction (PXRD) measurements were performed on a Panalytical X'pert PRO MPD X-ray diffractometer at 45 kV, 40 mA for Cu Kα (λ=1.5418 Å).

High resolution dynamic thermal gravimetric analysis (TGA) were performed under a continuous N2 flow and recorded on a TA Instrument Hi-Res TGAQ500 thermal gravimetric analyzer.

Water sorption experiments were carried out at different temperatures close to ambient (25° C.-45° C.) using a VTI-SA vapor sorption analyzer from TA Instruments (New Castle, Del., United States). The water vapor activity was controlled automatically by mixing wet vapor feed with a dry N2 line; hence, N2 acts as a carrier gas for water vapor. The sample "dry mass" was measured under N2 and was at equilibrium before introducing water vapor into the chamber. The adsorption isotherms, obtained at equilibrium, were collected within a range of 0%-95% RH.

Low pressure gas adsorption measurements were performed on a 3-Flex Surface Characterization Analyzer (Micromeritics) at relative pressures up to 1 atm. The cryogenic temperatures were controlled using argon baths at 87 K. The apparent surface areas were determined from the argon adsorption isotherms collected at 87 K by applying the Brunauer-Emmett-Teller (BET) and Langmuir models.

Homogenous microcrystalline samples of Y-shp-MOF-5 were activated by washing the as-synthesized crystals with 3×20 mL of DMF followed by solvent exchange in acetone for 3 days, during which the solution was refreshed several times. In a typical experiment, 30 to 40 mg of each activated sample was transferred (dry) to a 6-mm large bulb glass sample cell after being evacuated at room temperature using a turbo molecular vacuum pump and then gradually heated to 125° C. at a rate of 1° C./min, held for 16 h and cooled to room temperature.

Figure 9:
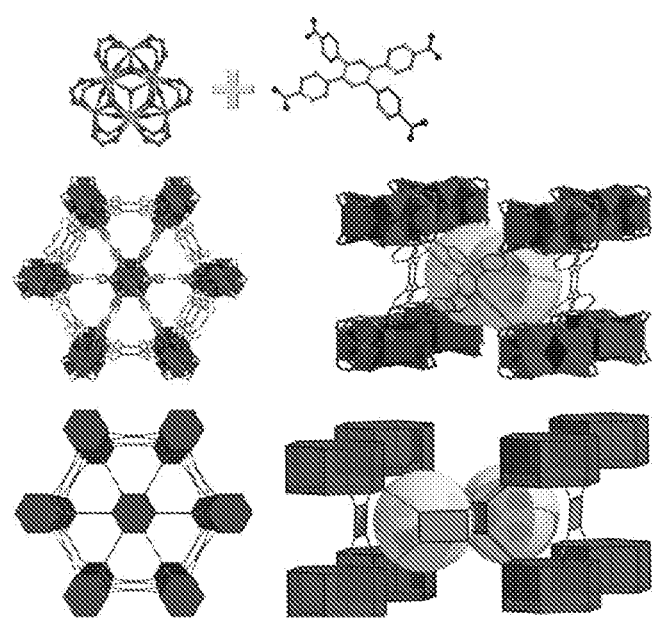
FIG. 9 illustrates a schematic representation of a Y-shp-MOF, according to some embodiments.

FIG. 9 illustrates a graphical representation of a Y-shp-MOF. In particular, at the top, FIG. 9 shows a crystal structure of Y-shp-MOF wherein a 4-connected ligand BTEB is assembled with a 12-connected rare earth nonanuclear MBB; and immediately below, in the middle of FIG. 9, the 3D framework with 1D triangular channels resulting from that assembly is shown. Finally, at the bottom of FIG. 9, the combination of hexagonal prism and rectangular building blocks results in a MOF with shp topology, which, as shown in FIG. 9, is augmented shp net.

Figure 10:
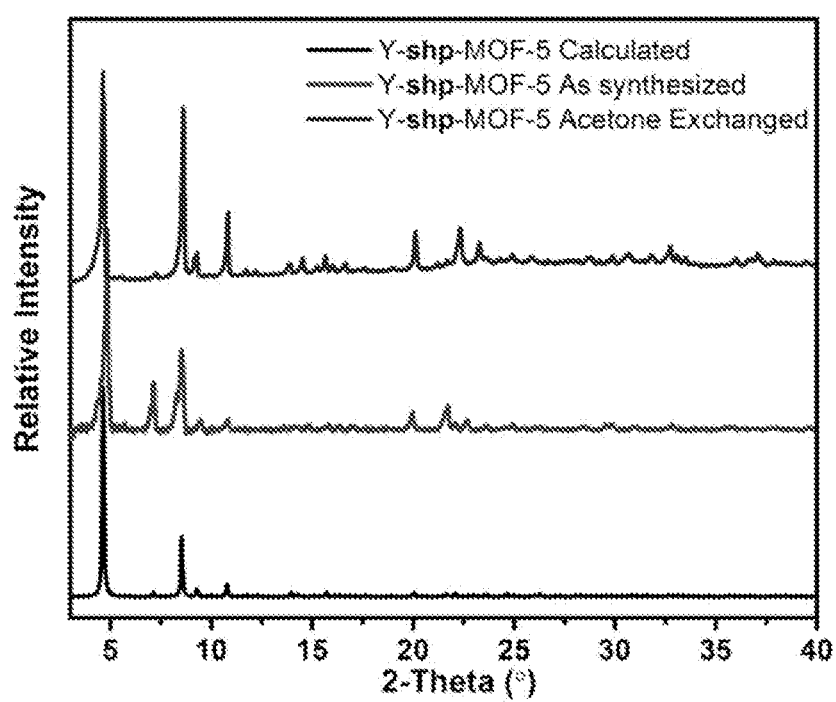
FIG. 10 is a graphical view of calculated and experimental PXRD patterns for Y-shp-MOF-5, indicating the purity of the as-synthesized and acetone exchanged samples, according to one or more embodiments of the present disclosure.
Figure 11:
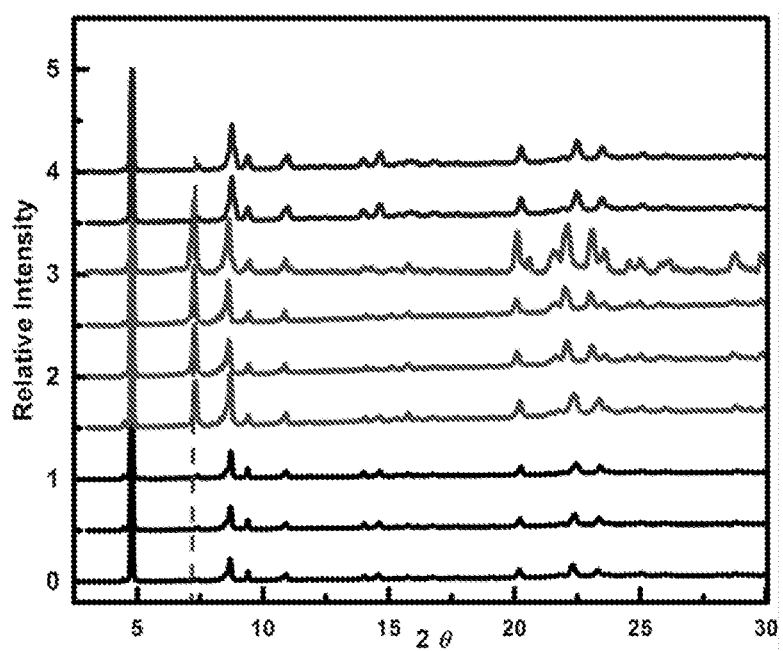
FIG. 11 illustrates a graphical view of powder X-ray diffraction patterns confirming the phase purity of Y-shp-MOF, according to some embodiments.

A solvothermal reaction involving an amount of 4-c, 1,2,4,5-tetrakis(4-carboxyphenyl)benzene (BTEB) reacted with an amount of $Y(NO_3)_3 \cdot 6H_2O$ in a N,N'-dimethylformamide (DMF)/water solution in the presence of an amount of 2-fluorobenzoic acid yields Y-shp-MOF. This solvothermal reaction resulted in transparent homogenous hexagonal-bipyramidal-shaped crystals. The in situ formation of the 12-connected (12-c) rare earth MBB was facilitated by the addition of excess 2-FBA which acts as a modulator for the in situ formation of highly connected polynuclear carboxylate-based clusters. The phase purity of the as-synthesized material and its stability in various solvents was confirmed by matching the as-synthesized powder X-ray diffraction (PXRD) pattern with the calculated one based on the crystal structure. FIG. 10. FIG. 11 illustrates a graphical view of powder X-ray diffraction patterns confirming the phase purity of Y-shp-MOF. PXRD also confirmed no significant changes in crystallinity of the material.

Figure 12:
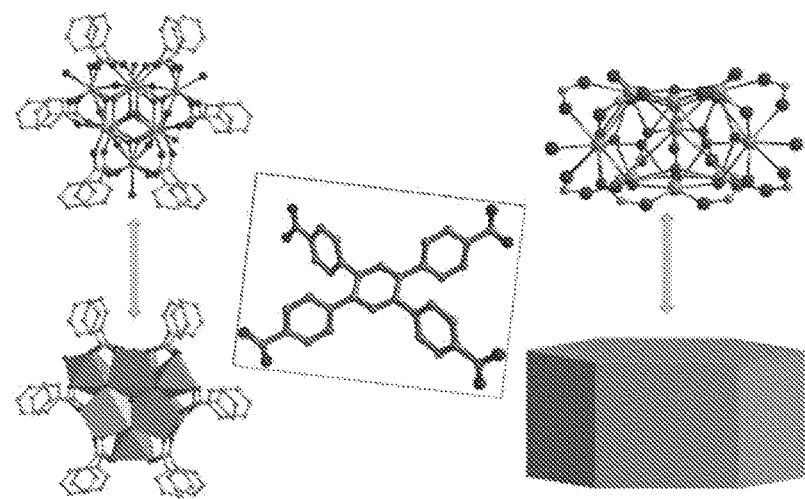
FIG. 12 is a schematic diagram of organic building blocks used in the construction of Y-shp-MOF-5 based on the 4-c organic linker 1,2,4,5-tetrakis (4-carboxyphenyl)benzene (BTEB) and 12-c carboxylate-based molecular building blocks (MBBs), according to one or more embodiments of the present disclosure.
Figure 13:
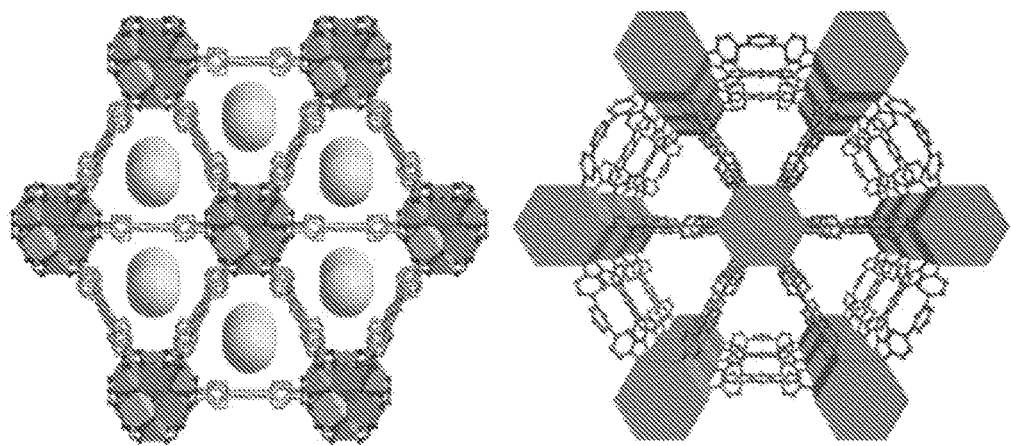
FIG. 13 is a schematic diagram showing the formation of RE-shp-MOF constructed from the assembly of BTEB and 12-c carboxylate-based MBB, which can be viewed as a rectangular and cuboctahedron node to afford the augmented shp net consisting of 1-D triangular channels (H atoms removed for clarity), according to one or more embodiments of the present disclosure.
Figure 14:
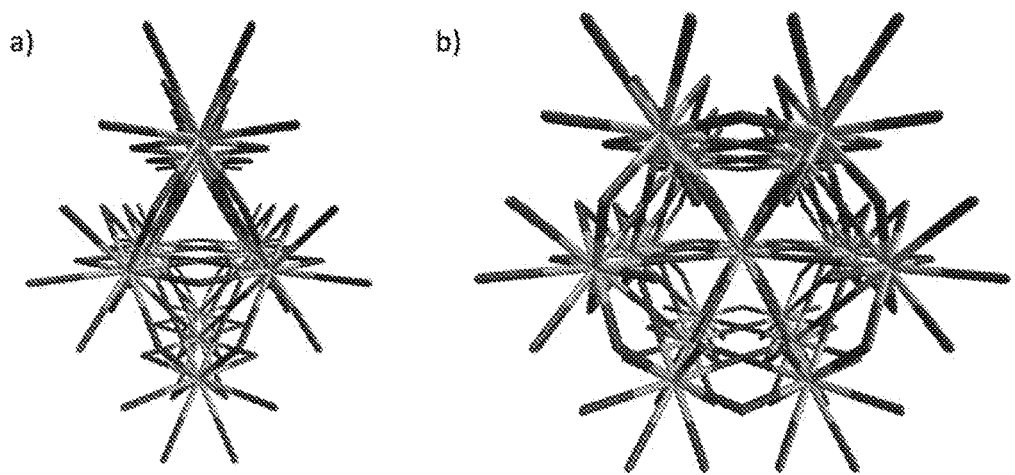
FIG. 14 is a schematic diagram of a topological analysis of Y-shp-MOF-5, a) each 12-c node (olive, with d6R vertex figure representative of the RE nonanuclear cluster) is connected to twelve 4-c nodes (purple); b) illustration of the shp-net connectivity and its view along the z-axis (Prior to topological analysis, the structure has been simplified to its basic nodes. The inorganic nonanuclear cluster is reduced to a 12-c node (α), while the tetratopic ligand is reduced to a 4-connected node (β). The RE-BTEB-MOF exhibits a (4, 12)-c shp topology. Point symbol for net: {4^36.6^30}{4^4.6^2}3 4, 12-c net with stoichiometry (4-c) 3(12-c); 2-nodal net; transitivity: [2133], shp topology), according to one or more embodiments of the present disclosure.
Figure 15:
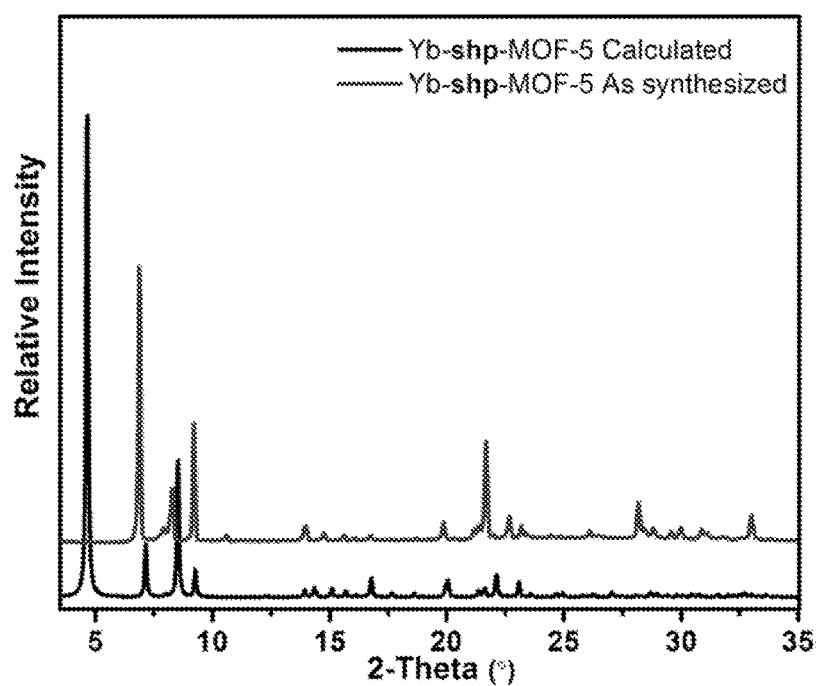
FIG. 15 is a graphical view of calculated and experimental PXRD patterns for Yb-shp-MOF-5, indicating the purity of the as-synthesized sample, according to one or more embodiments of the present disclosure.
Figure 16:
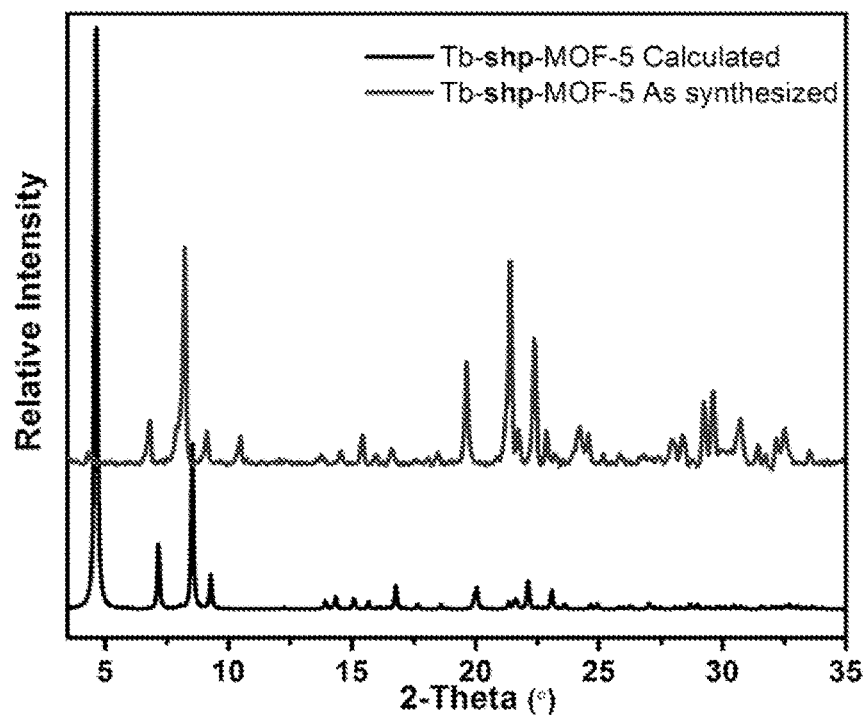
FIG. 16 is a graphical view of calculated and experimental PXRD patterns for Tb-shp-MOF-5, indicating the purity of the as-synthesized sample, according to one or more embodiments of the present disclosure.

Single-crystal X-ray diffraction (SCXRD) was used to characterize the structure of Y-shp-MOF. SCXRD shows that Y-shp-MOF crystallizes in the hexagonal space group P63/mmc and is characterized by the formula, $|DMAl_3[Y_9(\mu_3\text{-}O)_2(\mu_3\text{-}OH)_{12}OH_2(H_2O)_7(BTEB)_3].(solv)_x$ where DMA refers to dimethylammonium cation and solv refers to solvent. Topological analysis of the resulting crystal structure confirms that the obtained (4, 12)-connected MOF based on the distinct 12-connected polynuclear rare earth cluster $[Y_9(\mu_3\text{-}O)_2(\mu_3\text{-}OH)_{12}(H_2O)_7(O_2C\text{—})_{12}]$ linked through the rectangular-shaped BTEB ligand has the expected square hexagonal-prism shp topology. FIGS. 12, 13, and 14. The shp-MOF structure is based solely on linking nonanuclear Y carboxylate-based clusters. Y-shp-MOF is built from nonanuclear metal clusters enclosing nine yttrium cations ($Y_9$) statistically disordered over two positions and cluster arrangement in a tricapped trigonal prism, as shown in FIG. 9. Two crystallographically independent Y ions can be isolated; six of which coordinates to eight oxygen atoms; that is, two carboxylates of two separate ligands (BTEB), four $\mu_3$-OH, two $\mu_3$-O, and one water molecule to complete the coordination environment. Each of the remaining three Y ions coordinates to nine oxygen atoms; that is, four from carboxylates of four distinct BTEB ligands, four $\mu_3$-OH, and one terminal water molecule. The overall cluster is anionic $[Y_9(\mu_3\text{-}O)_2(\mu_3\text{-}OH)_{12}(O_2C\text{—})_{12}]\text{—}$, and the resultant overall charge of the framework is balanced by $DMA^+$ generated in situ upon the decomposition of DMF solvent molecules. As shown in FIG. 9, the shp network is composed of 12-connected nonanuclear cluster linked via 12 carboxylates from 12 different BTEB ligands to give a 12-connected MBB, hexagonal prism building unit. Y-shp-MOF structure can be viewed as a hexagonal close packing of the nonanuclear cluster MBBs and thus can be further simplified as pillared hexagonal (hxl) layers; thus forming uniform triangular 1D channels of 12 Å along c axis. Different RE metal (i.e., Yb and Tb) analogues have been isolated under similar reaction conditions. FIGS. 15 and 16.

Figure 17:
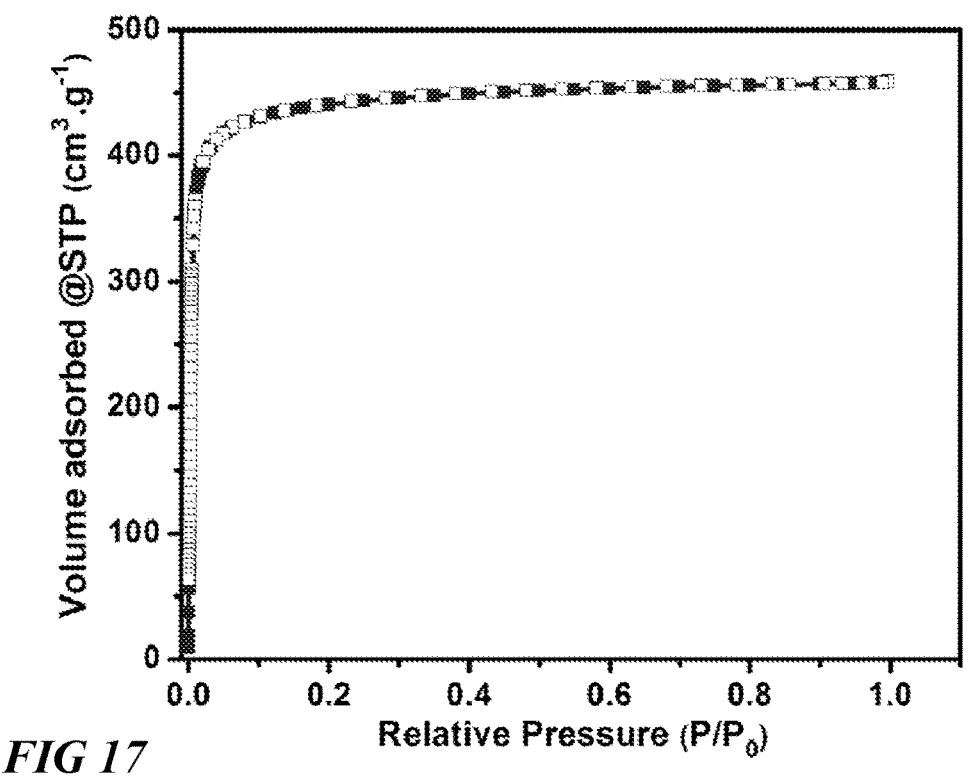
FIG. 17 is a graphical view of Ar adsorption isotherm for Y-shp-MOF-5 collected at 87 K. Adsorption and desorption profiles are shown in closed and open symbols, according to one or more embodiments of the present disclosure.
Figure 18:
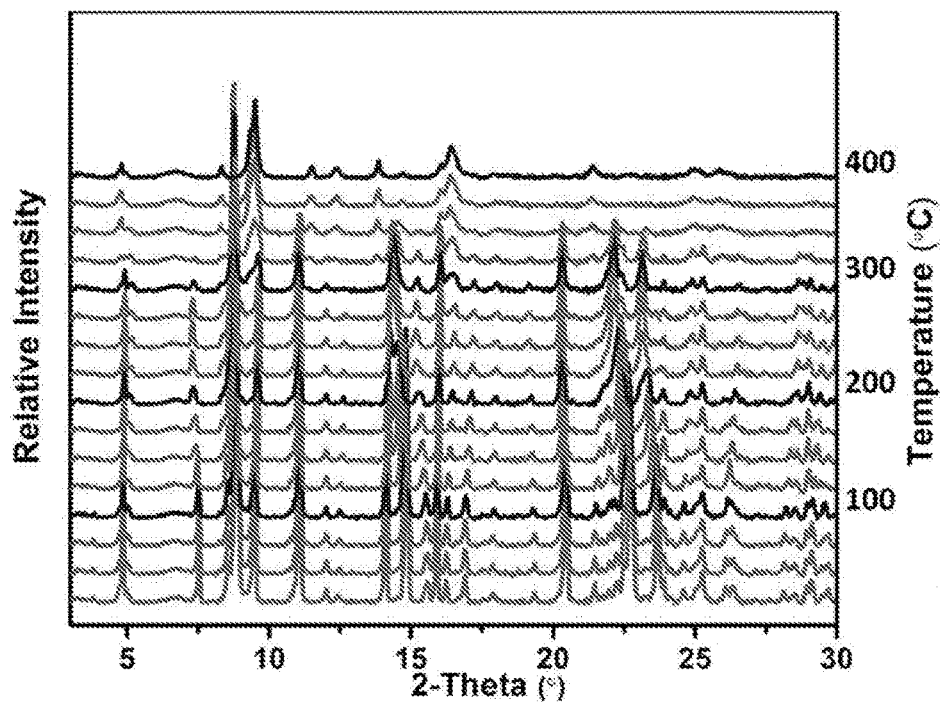
FIG. 18 is a graphical view of a VT-PXRD for acetone exchanged samples showing Y-shp-MOF-5 retaining crystallinity up to 400° C., according to one or more embodiments of the present disclosure.
Figure 19:
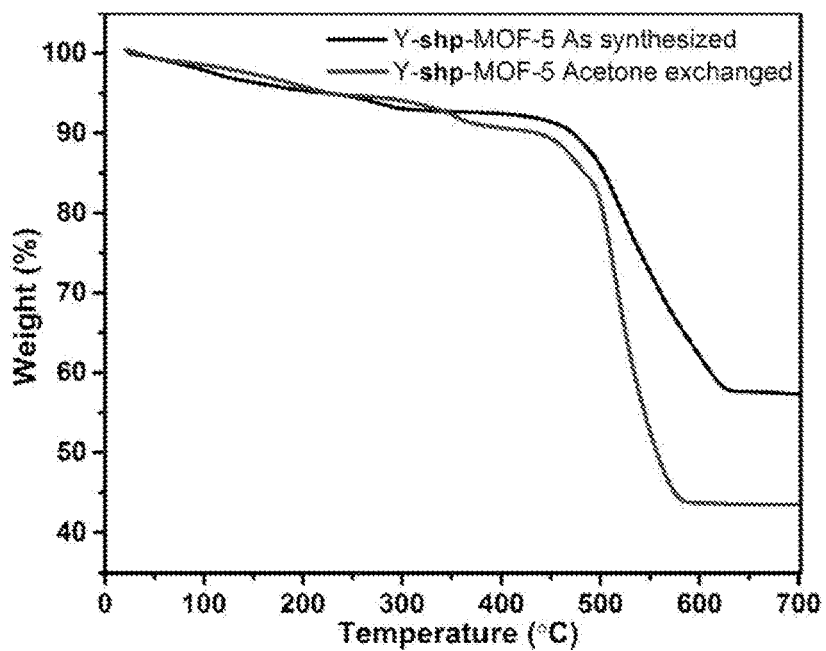
FIG. 19 is a graphical view of thermal gravimetric analysis plot of the as-synthesized and acetone exchanged Y-shp-MOF-5, according to one or more embodiments of the present disclosure.

To explore the porosity of Y-shp-MOF structure, acetone exchanged samples were activated by heating to 125° C. under vacuum. An Ar adsorption study at about 87 K showed a fully reversible Type-I isotherm, characteristic of a microporous material with permanent microporosity. FIG. 17. The apparent BET surface area and the total pore volume were estimated to be about 1550 $m^2g^{-1}$ and about 0.63 $cm^3$ $g^{-1}$, respectively. The pore volume was in good agreement with the theoretical value derived from SCXRD data of 0.61 $cm^3\ g^{-1}$. Markedly, the Y-shp-MOF-5 structure preserved its optimal porosity after heating up to about 160° C. and structural integrity as confirmed by variable temperature (VT) PXRD and thermal gravimetric analysis (TGA). FIGS. 18 and 19.

Figure 20:
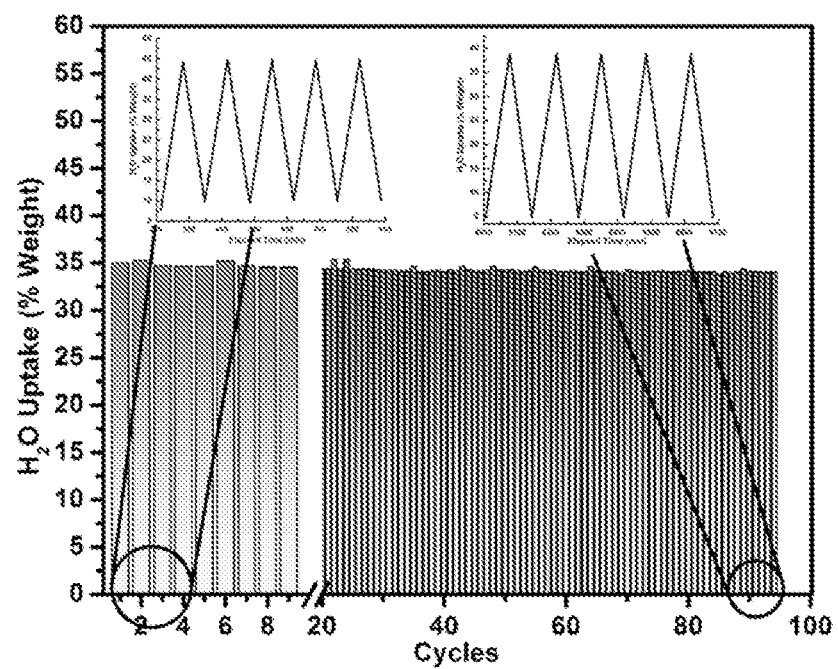
FIG. 20 illustrates a graphic view of the change in total mass variation of Y-shp-MOF during non-equilibrium adsorption and desorption over 200 cycles at various amounts of relatively humidity, according to some embodiments.
Figure 21:
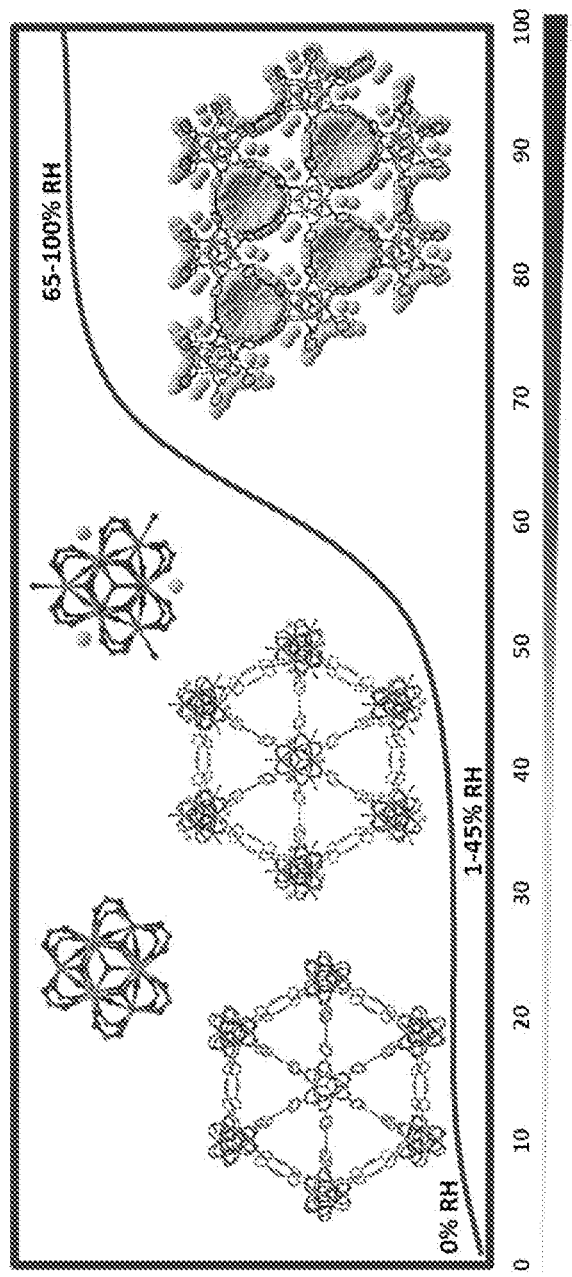
FIG. 21 illustrates a graphical view of the adsorption sites of water molecules in Y-shp-MOF at relative humidity ranges from 0% to 100%, according to some embodiments.

In light of the large number of exposed open metal sites per nonanuclear cluster, ascertained from the crystal structure, FIGS. 20 and 21 illustrate the performance of the Y-shp-MOF-5 under different relative humidity levels by performing water adsorption measurements and collecting crystal structures under variable relative humidity conditions. In particular, FIG. 20 illustrates the change in total mass variation of the Y-shp-MOF-5 during non-equilibrium adsorption and desorption over 200 cycles driven by a change in relative humidity and indicating various amounts of $H_2O$ uptake at various amounts of relative humidity. FIG. 21 illustrates the adsorption sites of water molecules in Y-shp-MOF with exposure to elevated relative humidity. At 0% RH, no water molecules are observed; between 1% RH and 45% RH, water molecules occupy open metal sites; and above 65% RH water molecules occupy triangular channels.

Figure 22:
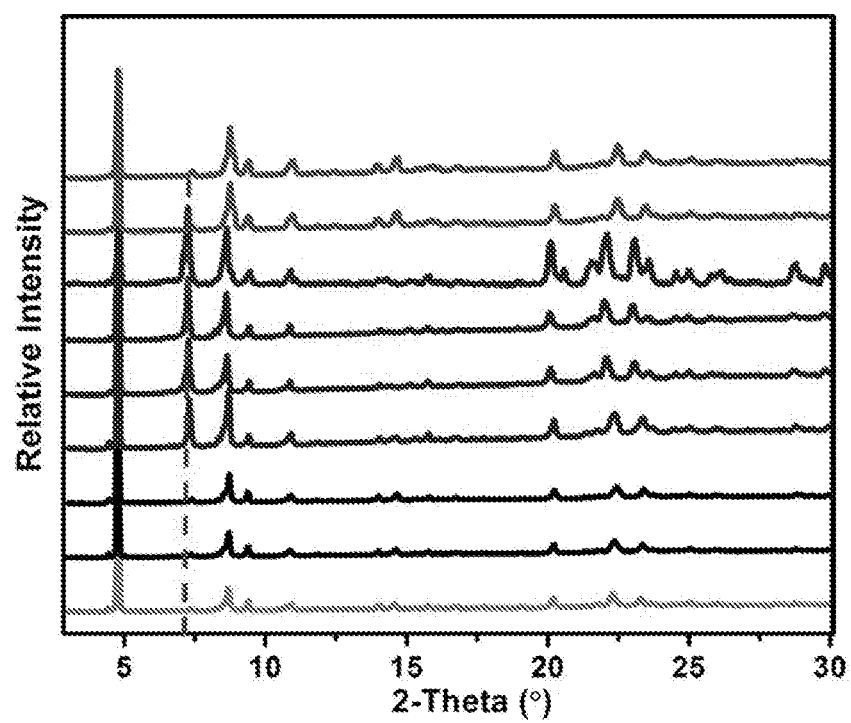
FIG. 22 is a graphical view of variable relative humidity PXRD collected on acetone exchanged Y-shp-MOF-5 sample exposed to elevated relative humidity levels: At ambient conditions (—) below 65% RH (—) above 65% RH up to 95% RH (—) less than 50% RH (——) according to one or more embodiments of the present disclosure.
Figure 23:
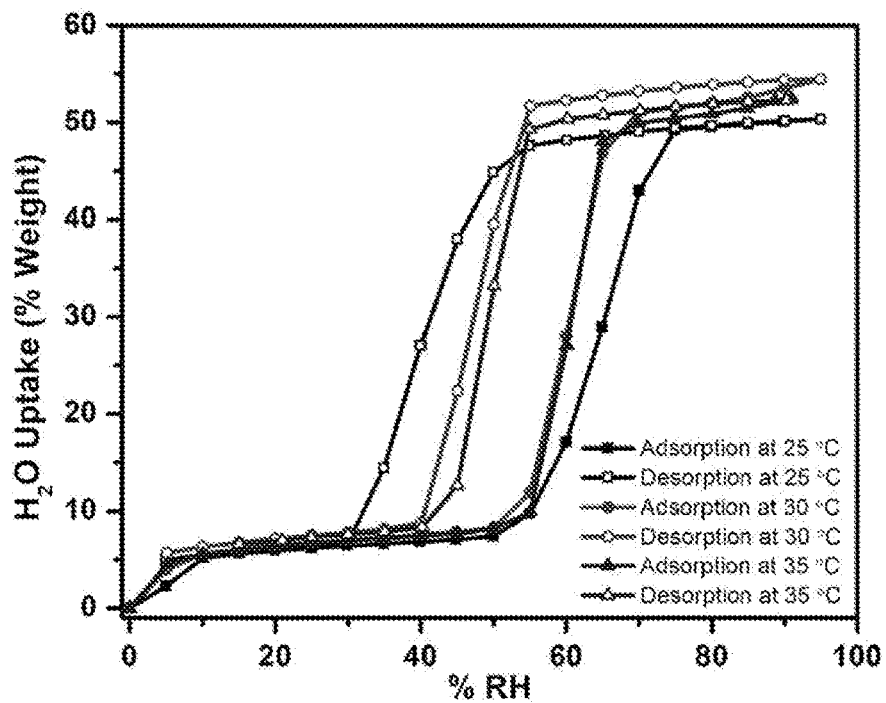
FIG. 23 is a graphical view of water vapor adsorption isotherms of acetone exchanged samples of Y-shp-MOF-5 activated at 125° C. and collected at 25° C., 30° C. and 35° C. showing similar behavior to the one collected at 25° C. with slight reduction in the working range for moisture level control, according to one or more embodiments of the present disclosure.

Water Adsorption Properties of Y-Shp-MOF-5. Water vapor adsorption experiments were carried out to examine the water vapor adsorption characteristics of the Y-shp-MOF-5 using a VTI-SA vapor sorption analyzer from TA Instruments (New Castle, Del., United States). The water vapor partial pressure was controlled automatically by mixing wet vapor feed with a dry $N_2$ line; hence, $N_2$ acts as a carrier gas for water vapor. Pre-drying of the sample was carried out at about 125° C. in the presence of $N_2$ dry carrier. The sample "dry mass" was measured under $N_2$ and was at equilibrium (at about 25° C.) before introducing water vapor into the chamber. The Y-shp-MOF-5 stability to water was confirmed by in situ powder X-ray diffraction (PXRD) data under different humidity conditions (0%-95%). FIG. 22. The adsorption isotherms, obtained at equilibrium, were collected between about 0% RH and 95% RH at temperatures close to ambient (25° C.-35° C.) at different activation temperatures. FIG. 23. In addition, in order to evaluate the hydrothermal stability of the material, the sample was exposed to few 100-continuous water adsorption and desorption cycles.

Figure 24:
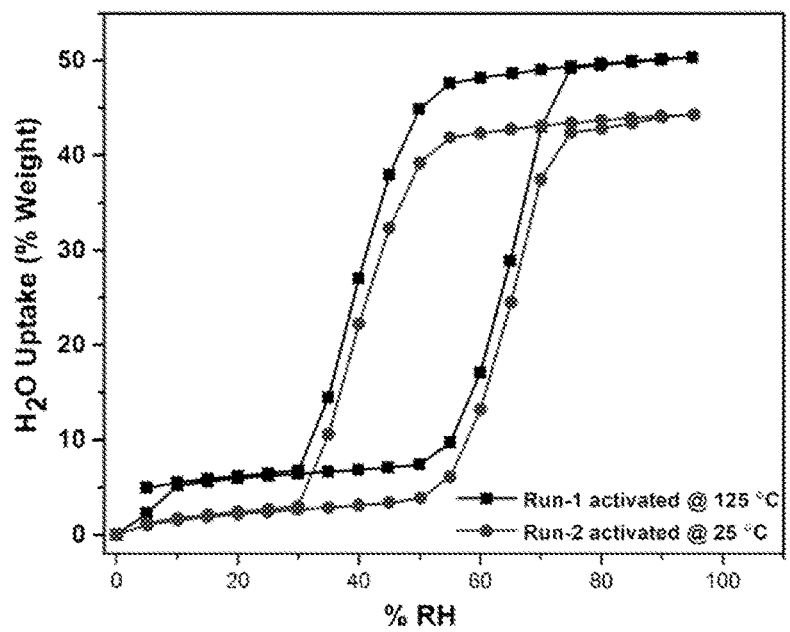
FIG. 24 illustrates a graphical view of H₂O isotherms for a Y-shp-MOF at various activation temperatures indicating H₂O uptake at various amounts of relative humidity, according to some embodiments.
Figure 25:
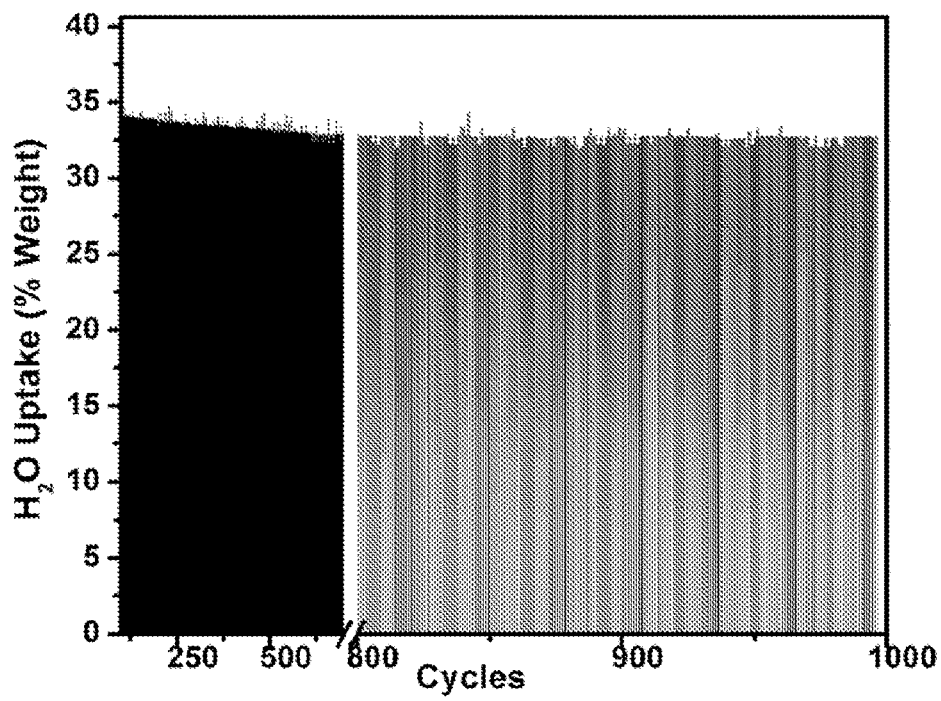
FIG. 25 is a graphical view of change of total mass variation of Y-shp-MOF-5 during non-equilibrium adsorption and desorption over more than 1000 cycles driven by the repetitive change in relative humidity between 25% RH and 85% RH, according to one or more embodiments of the present disclosure.

Condensation Pressure and Uptake Capacity: FIG. 24 is a graphical view of $H_2O$ isotherms for a Y-shp-MOF at various activation temperatures indicating $H_2O$ update at various amounts of relative humidity. In particular, FIG. 24 illustrates the water isotherms of Y-shp-MOF for water adsorption and desorption collected after activating a sample at 125° C. and for water adsorption and desorption collected after activating a sample at 25° C.

The water vapor adsorption isotherm of the Y-shp-MOF activated at 125° C., measured gravimetrically at 25° C. is shown in FIG. 24, with the black or darker data points. The water vapor adsorption isotherm of the fully activated (at about 125° C.) Y-shp-MOF-5 revealed an initial water uptake of 5 wt %. at low % RH (<20% RH), after which it plateaus until % RH reaches 55%-60%, where it exhibits a steep uptake until 85% RH leading to a total uptake capacity of 50 wt % at equilibrium. The exposed Y open metal sites served as the primary preferable adsorption sites for water molecules at low % RH. At higher moisture levels, a steep water vapor uptake was observed as the uptake capacity of Y-shp-MOF-5 reached 50 wt %, followed by a plateau at 85% RH, FIG. 24 (black circles). The overall water adsorption isotherm profile revealed an interesting s-shaped (sigmoidal) adsorption and desorption branches with the full desorption completed at intermediate relative humidity (30% RH) with an associated total working capacity equivalent to 45 wt %.

As shown in FIG. 24, the water molecules, at low pressure, are adsorbed on the unsaturated open metal sites. The limited water uptake at lower pressure, as illustrated by the step, indicates that the affinity of water to the MOF surface is low. This is related to the hydrophobicity of the ligand; therefore, higher water vapor pressure is required to induce the pore filling.

Y-shp-MOF has a remarkable water vapor adsorption isotherm showing a hysteresis loop with inflection points of adsorption and desorption branches at about 0.55 and 0.45 of $p/p_0$ respectively.

The type IV-like adsorption/desorption isotherms with corresponding inflection points of adsorption and desorption branches at $p/p_0$ of about 0.55 and 0.45, respectively, as depicted in FIG. 24. Remarkably, this unique shape of the water vapor adsorption isotherm (i.e. steep adsorption at 55% RH-60% RH and a pronounced hysteresis), unusual for microporous materials, concurs with the recommended working range for the moisture level control (40% RH-60% RH), desired for the preservation of comfortable moisture levels in confined spaces and conform to the standards set by occupational health and safety, aerospace and aviation agencies nationally and internationally.

In order to differentiate between the water molecules molecules adsorbed on the open metal sites and those filling the remainder of the pore system, a $2^{nd}$ cycle of water vapor adsorption-desorption measurements (red circles) were carried out without any pre-activation or heating. As shown in FIG. 24 (red circles), a slight decrease in the total water uptake by nearly 5 wt % was observed but with a preserved total water working capacity of about 45 wt %, corresponding to the total water uptake at saturation of 45 wt %. The water desorption was governed solely by changes/reduction in the relative humidity, suggesting that the complete desorption of non-coordinated water molecules occurred due to the relatively weak water/framework interactions. Conversely, the coordinated water molecules to the nonanuclear cluster could not be desorbed simply by reducing the relative humidity below 30% RH, signifying their relatively strong interaction with the open metal sites and the requisite for an external stimuli/driving force such as heat for their displacement. Hence, the initial step in the water vapor adsorption isotherm for the fully activated Y-shp-MOF-5 (at 125° C.), followed by the first plateau corresponding to a water uptake of 5 wt % was associated with the coordination of water molecules to the available open metal sites in the cluster, regarded as the most energetic sites for the initial adsorption of water molecules.

To further delineate the unique water adsorption properties associated with the Y-shp-MOF-5 and assess the effect of the temperature on the moisture-control working range, additional water adsorption studies were performed at temperatures close to ambient conditions (i.e., 30° C. and 35° C.). As shown in FIG. 23, for the samples collected at 25° C., a similar behavior and isotherm shape was observed, but with a relatively steeper uptake at 55% RH and a prompt attainment of the plateau at a lower humidity level of 65% RH, instead of 80% RH, for samples collected at 25° C. Noticeably, the desorption of the non-coordinated water molecules, occurred at a relatively higher humidity level of 40% RH. Consequently, the Y-shp-MOF-5 associated working range for the moisture level control was slightly reduced with increasing the temperature.

In principle, the concept of moisture control devices using adsorbents implied that the same material can adsorb and desorb water vapor as it was exposed to different levels of humidity as environmental triggers. However, most materials lacked this duality, as they either adsorbed water or desorbed water vapor to the environment under specific conditions. Principally, the deployment of the Y-shp-MOF-5 into moisture control devices offered vital advantages as it permitted an adsorbing moisture starting at a humidity level of 50% RH and promptly released water when the humidity level went below 45% RH. Using the appropriate amount of Y-shp-MOF-5/volume of space: i) the Y-shp-MOF-5 adsorbent kept adsorbing water vapor until the RH dropped below 45% or the material reached its saturation capacity of 50 wt % of moisture; and ii) the Y-shp-MOF-5 adsorbent started releasing the adsorbed water molecules into the atmosphere bringing the humidity back to a comfortable level, when the humidity levels decreased below a comfortable level that is below 40% RH.

Figure 26:
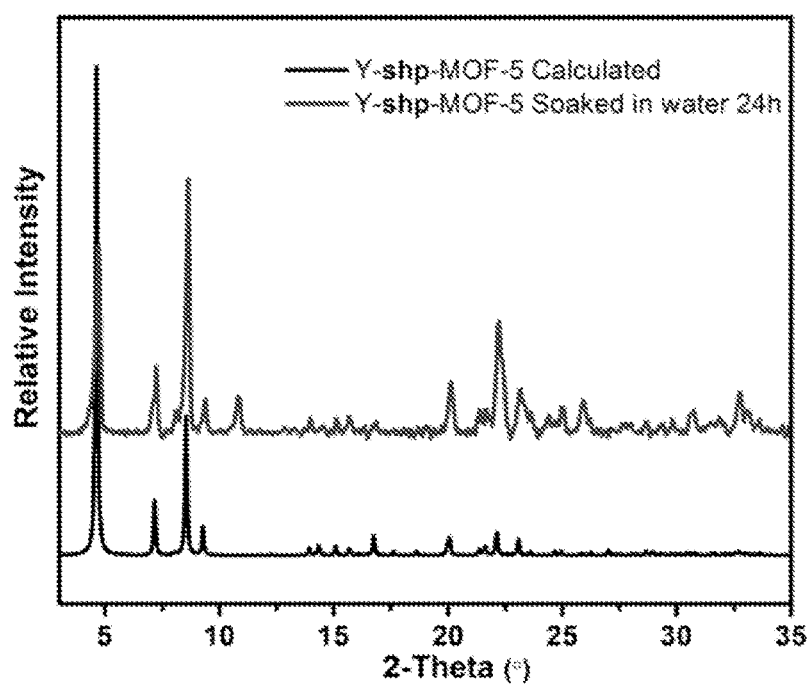
FIG. 26 is a graphical view of calculated and experimental PXRD patterns for Y-shp-MOF-5, indicating the stability of the acetone exchanged samples after soaking in water for 24 h, according to one or more embodiments of the present disclosure.
Figure 27:
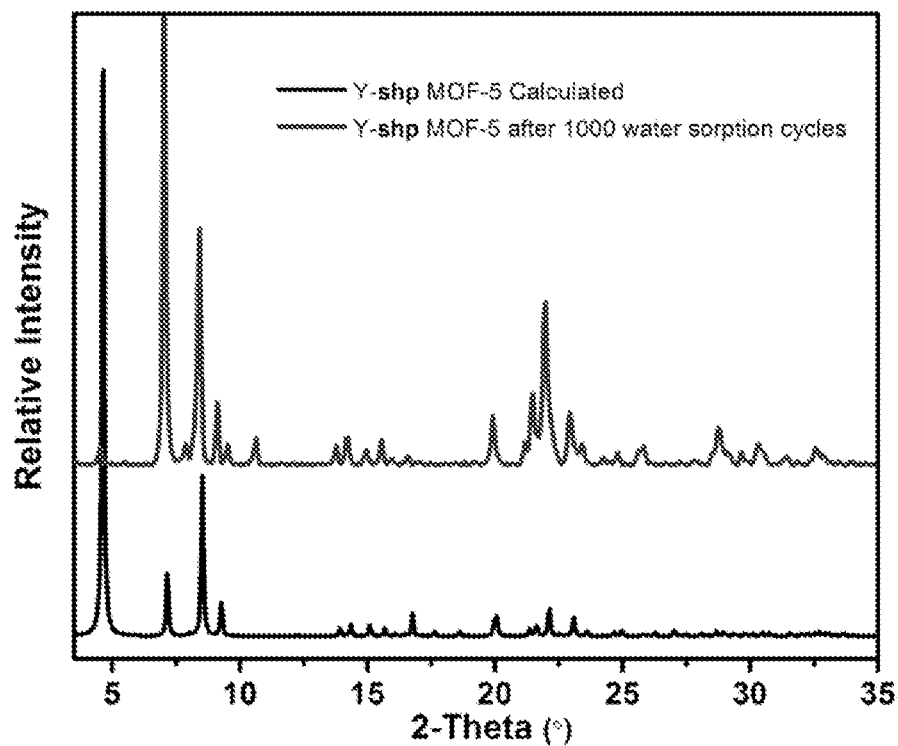
FIG. 27 is a graphical view of calculated and experimental PXRD patterns for Y-shp-MOF-5, indicating the stability of the acetone exchanged samples after soaking in water for 24 h, according to one or more embodiments of the present disclosure.
Figure 28:
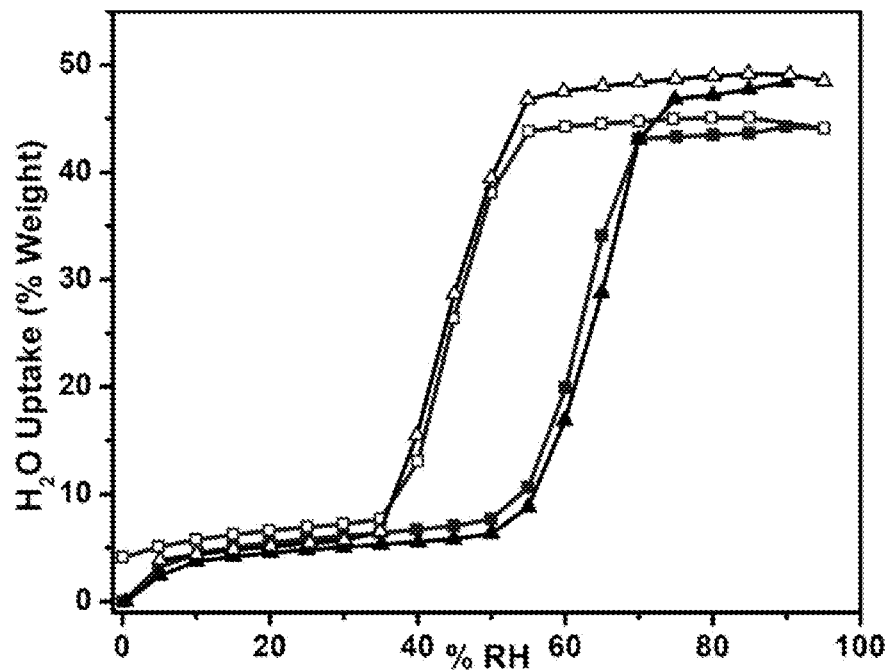
FIG. 28 is a graphical view of water vapor adsorption isotherms of (▲) freshly prepared acetone exchanged sample (both activated at 125° C.) of Y-shp-MOF-5 and (✶) after exposing the sample to 1000 water sorption cycles. The full and the empty symbols reflect the adsorption and desorption, respectively, according to one or more embodiments of the present disclosure.

Further, cyclic measurements were conducted on the Y-shp-MOF-5 to evaluate the cyclic adsorption/desorption performance of the material. More than 1000 water vapor adsorption and desorption measurements, at room temperature and non-equilibrium conditions, were performed on the Y-shp-MOF-5 (FIG. 20, 25) with the adsorption at 85% RH (26 mbar) and the desorption at 25% RH (8 mbar). Prior to exposing the sample to numerous cycles, acetone exchanged sample was soaked in liquid water. The stability of the sample was monitored with PXRD over the course of 24 h (FIG. 26). The Y-shp-MOF-5 showed a high and a steady cyclic water vapor adsorption operation as it maintained its working capacity in the adequate range of 35 wt %-40 wt %. The PXRD patterns and the water adsorption isotherm collected (FIGS. 27 and 28) on the extensively recycled Y-shp-MOF-5 confirmed the hydrolytic stability of the Y-shp-MOF-5 and the maintenance of its structural features and original adsorption properties.

Figure 29:
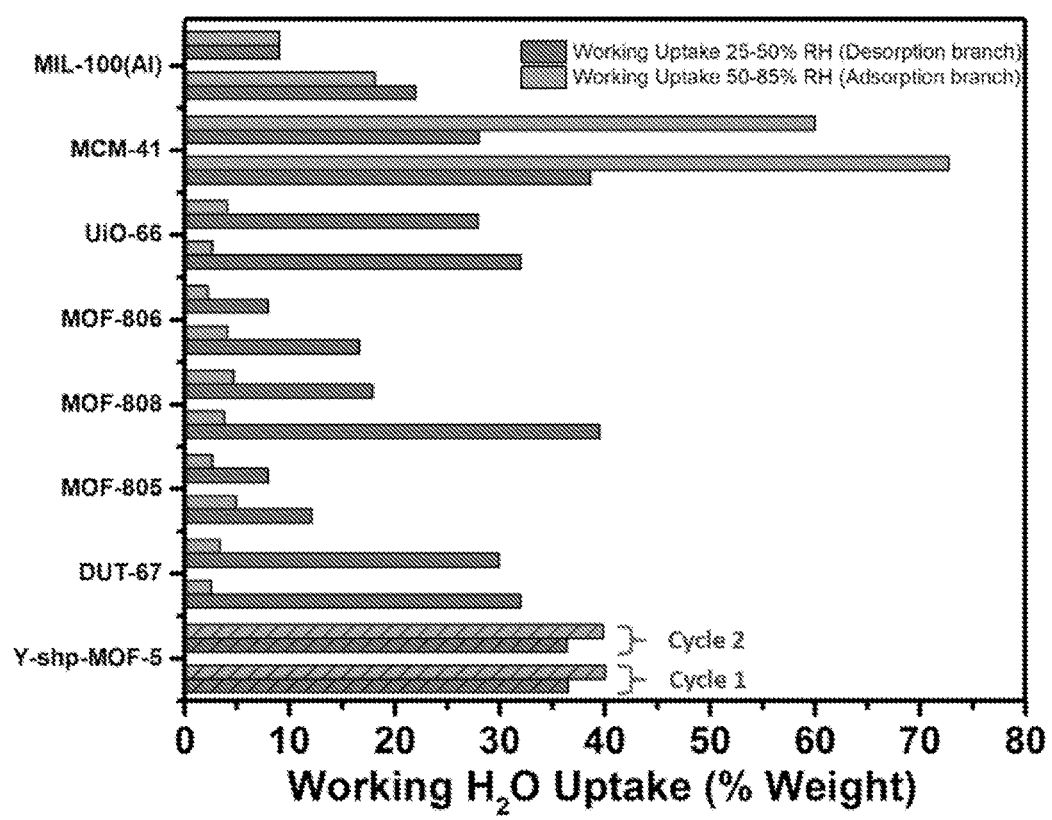
FIG. 29 is a plot of two isothermal cycles of water vapor uptakes and release at 25 C for selected best materials as compared to Y-shp-MOF-5 calculated from the adsorption and desorption branches between 50-85% RH and 50-25% RH, respectively, according to one or more embodiments of the present disclosure.
Figure 30:
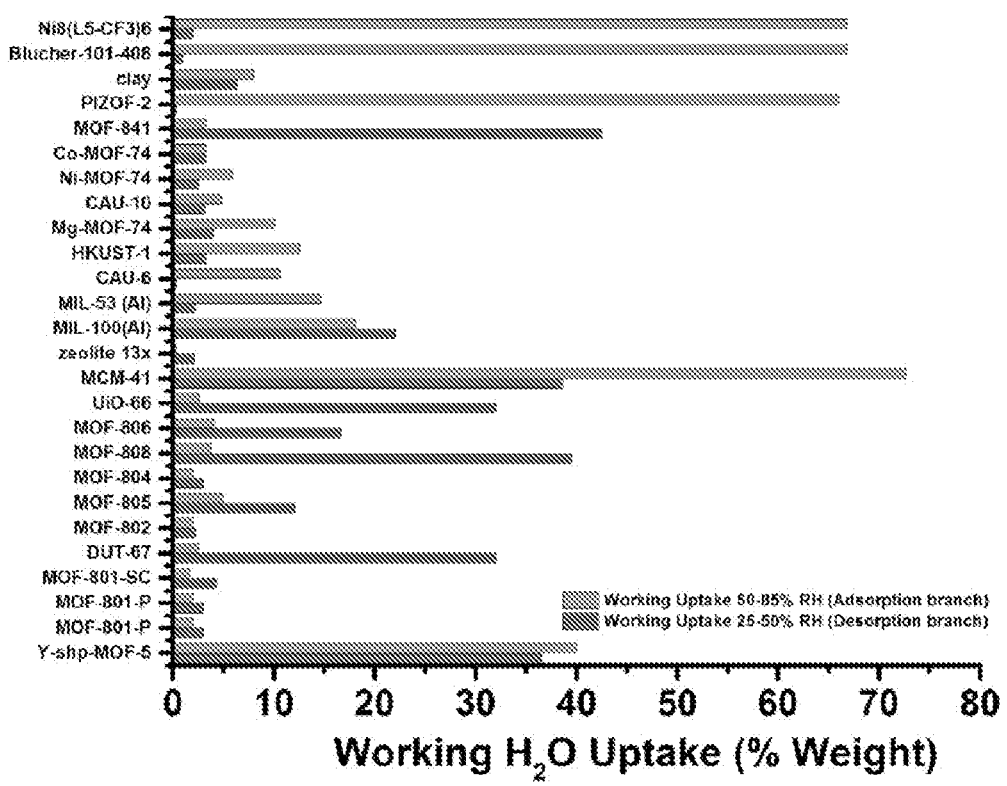
FIG. 30 is a plot of water vapor uptakes and release at 25° C. best materials as compared to Y-shp-MOF-5, calculated from the adsorption and desorption branches between 50-85% RH and 50-25% RH, according to one or more embodiments of the present disclosure.

In order to illustrate the uniqueness of Y-shp-MOF-5 for moisture control, all the materials in the literature with reported water vapor adsorption and desorption branches were examined and compared to Y-shp-MOF-5 according to scrutinized technical requirement for indoor moisture control. A suitable material for moisture control related applications exhibited the following features: (i) S-shaped water vapor adsorption isotherms with adsorption and desorption branches separated in the 40-60% RH range and (ii) high water vapor uptake from the adsorption branch between 50% and 85% RH equal to the amount of water vapor released (extracted from desorption branch) from 50% RH down to 25% RH. These features reflected the (a) the requirement from adsorption-desorption shape and (b) how optimum was the RH % (water vapor pressure) gradient between adsorption and desorption, to ensure suitable adsorption swing for moisture control operations. FIG. 29 shows two isothermal cycles of water vapor uptakes and release at 25° C. for selected best materials as compared to Y-shp-MOF-5, calculated from the adsorption and desorption branches between 50-85% RH and 50-25% RH, respectively. The corresponding data for other water vapor adsorbents is shown in FIG. 30. Y-shp-MOF-5 showed a unique combination of high, equal and steady adsorption uptakes and release in the specific range RH % (vapor pressure) tailored for moisture control operations, as compared to water vapor adsorbent reported to date.

In situ SCXRD study on the Y-Shp-MOF-5 at different humidity level: The X-ray diffraction data for the as synthesized structure as well as for the activated structure at 125° C. were measured on a Bruker X8 PROSPECTOR APEX II CCD diffractometer (Cu Kα λ=1.54178 Å). The X-ray diffraction data for the 22% and 100% RH were collected on a Bruker APEX II Duo CCD diffractometer using Mo Kα radiation (λ=0.71073 Å). Indexing was performed using APEX2 (Difference Vectors method). Data integration and reduction were performed using SaintPlus 6.01. Absorption correction was performed by multi-scan method implemented in SADABS. Space groups were determined using XPREP implemented in APEX2. The structure was solved using SHELXS-97 (direct methods) and refined using SHELXL-2013 (full-matrix least-squares on $F^2$) contained in APEX2, WinGX v1.70.01 and OLEX2.

All four crystal structures of Y-shp-MOF-5 crystallize in the hexagonal crystal system in the space group $P6_3/mmm$. Crystal data and refinement conditions are shown in Tables S3-S6. The nonanuclear (Y9) clusters are disordered over two positions with occupancy factors of 0.79, 0.70, 0.74 and 0.71 for structures 1, 2, 3 and 4, respectively. To refine them properly, thermal parameters of all chemically equivalent atoms and distances between them were constrained/restrained to be the same. Since light oxygen atoms O3 at one cluster orientation were located close to heavy yttrium Y2 atoms at the second cluster orientation, their thermal parameters were constrained to be the same. In the as synthesized structure 1, oxygen atoms at the axial positions of the nonanuclear cluster reveal elongated thermal ellipsoids and were split into 2 positions and refined with the same thermal parameters as one hydroxyl group and two water molecules at the each side of the cluster. Therefore, three dimethylammonium cations are needed to balance the framework charge and then the formula of 1 is |DMA|$_3$[Y$_9$(µ$_3$-O)$_2$(µ$_3$-OH)$_{12}$(OH)$_2$(H$_2$O)$_7$(BTEB)$_3$]. (solv)$_x$ (DMA$^+$=dimethylammonium cation and solv=solvent). The dimethylammonium cations, disordered over 12 positions, were localized for the major part of the disorder only. The anisotropic refinement of DMA$^+$ cations was unstable, so they were refined with a fixed geometry in an isotropic approximation.

In activated (2) and both hydrated structures (3 and 4), thermal ellipsoids of oxygen atoms at the axial positions of the nonanuclear cluster were similar to other oxygen atoms in the structures. Nevertheless, the ICP measurements of activated Na$^+$-exchanged sample confirm the same 1:3 relationship between outer cations and Y$^{3+}$ as for 1. Therefore, the dimethylammonium cations were localized for the major part of the disorder only and refined isotropically with a restrained geometry for crystal structures 2-4. It was not possible to use SQUEEZE procedure to estimate crystal composition for the structures 1-4 due to considerable disorder of the framework.

Figure 31:
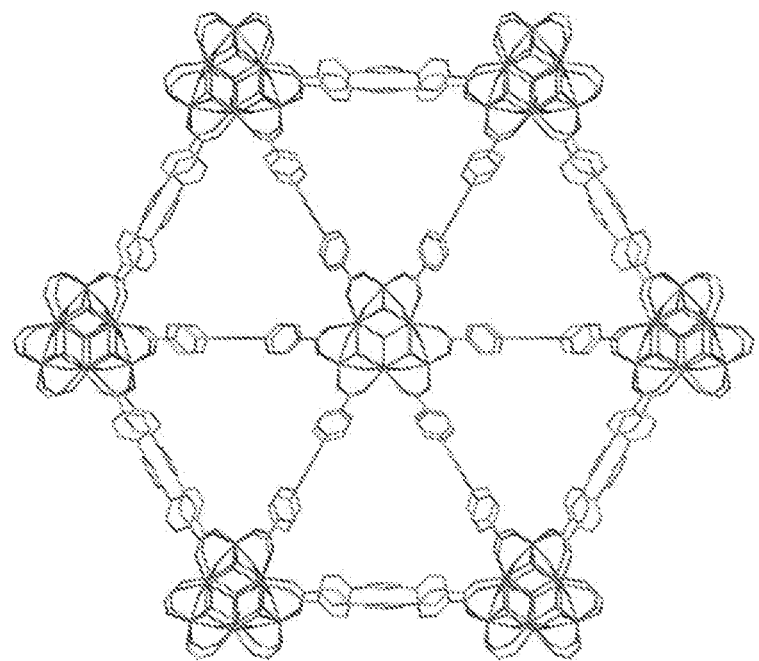
FIG. 31 is a schematic diagram of residual electron density ($F_o$-$F_c$) maps of the crystal structure of 2, clear even at the iso-surface level −0.5 e, according to one or more embodiments of the present disclosure.
Figure 32:
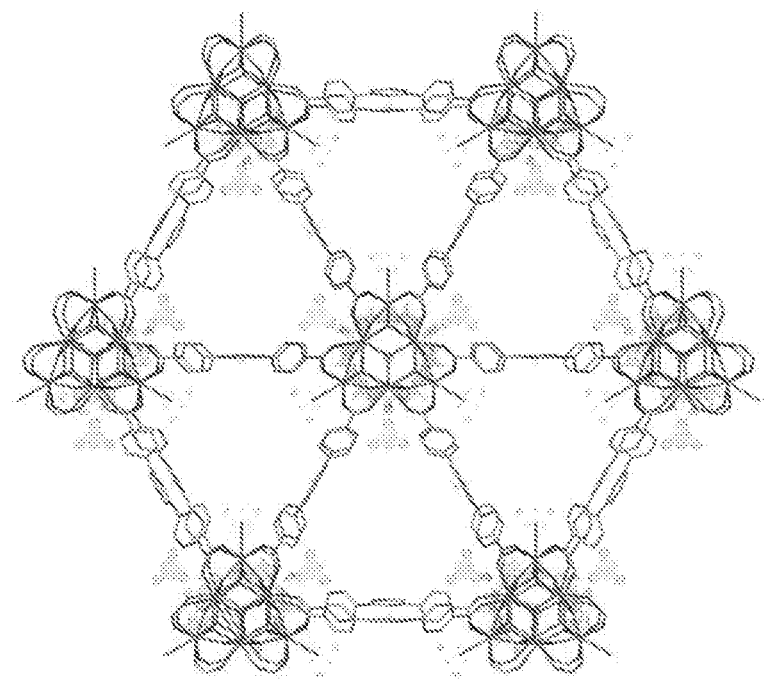
FIG. 32 is a schematic diagram of residual electron density ($F_o$-$F_c$) maps of the crystal structure of 3 at the iso-surface level −1.3 e, according to one or more embodiments of the present disclosure.
Figure 33:
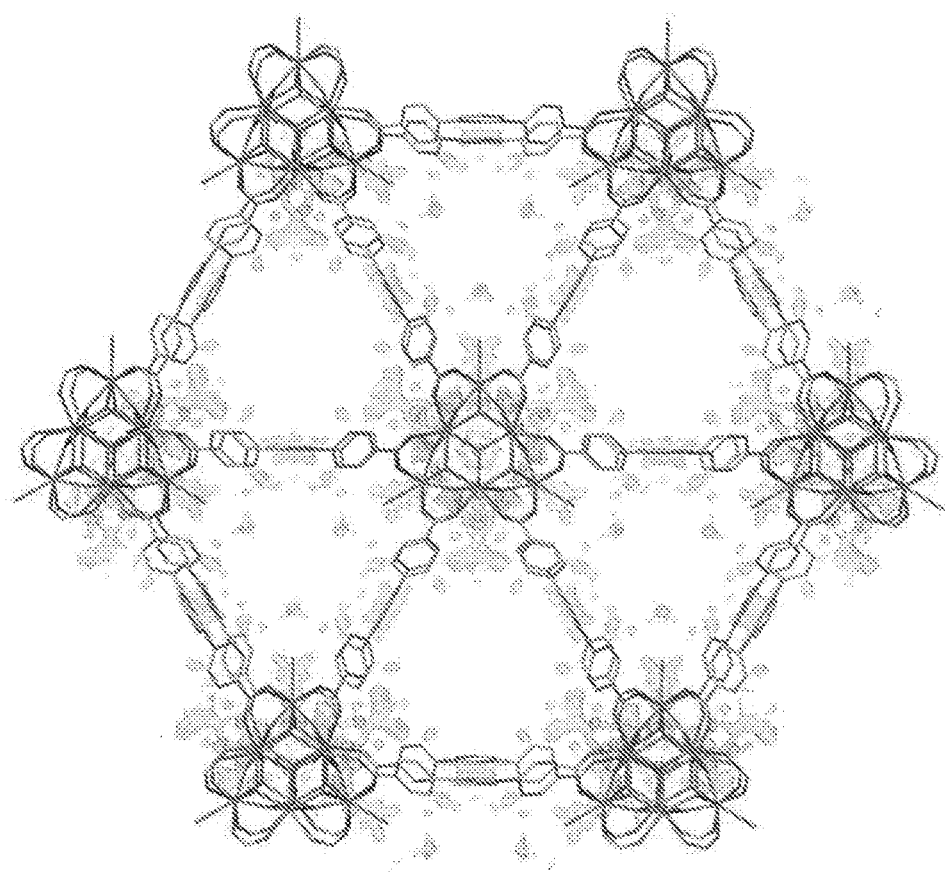
FIG. 33 is a schematic diagram of residual electron density ($F_o$-$F_c$) maps of the crystal structure of 4 at the iso-surface level −1.3 e, according to one or more embodiments of the present disclosure.

Additionally, in order to gain a better insight and elucidate the mechanism governing this unique water vapor adsorption-desorption behavior, in situ SCXRD measurements were carried out on crystals exposed to various relative humidity levels (FIG. 29). SCXRD data collected for the guest-free (0% RH) Y-shp-MOF-5 structure and the corresponding ones at 22% RH and 100% RH showed clearly that the crystal structure remained intact when exposed to different water vapor partial pressures. Prior to studying the preferred water adsorption sites, diffraction data for a crystal mounted in an environmental gas-cell was collected and evacuated in situ under dynamic vacuum at 125° C. for 12 hours (2). Certainly, no significant residual electron density was found in the difference Fourier maps in the pores or around the cluster, FIG. 31, indicating the anticipated removal of the coordinated water molecules as well as the absence of free guest water molecules in the pore system and confirming the presence of at least three exposed open metal sites per RE cluster. In addition, thermal parameters associated to the O-atoms at the axial positions suggested that hydroxyl groups coordinate to the cluster. Subsequently, the fully activated crystal was exposed to 22% RH (3) and 100% RH (4) by using saturated potassium acetate solution and a drop of water respectively. After 24 h equilibration, new set of data were collected 3 and 4. Crystallographic analysis of 3 reveals that the open metal sites present in 2 were now fully occupied by water molecules. Diffuse electron density around the cluster suggested the presence of some water molecules hydrogen bonded with the hydroxyl groups of the cluster (FIG. 32). In 4, exposed to 100% RH at 25° C., apart from water molecules and electron density observed in 3, considerable diffused electron density was observed in the channels and the most ordered water molecules can be localized (FIG. 33). The partial order of the water molecules at higher relative humidity was also supported by the PXRD data (FIG. 22). Nevertheless, most of the observed electron density as water molecules could not be crystallographically modeled due to the non-ordered nature of the adsorbed water molecules in the pore system of the Y-shp-MOF-5.

SCXRD experiments (FIG. 21) confirmed that the crystal structure remained unaltered when exposed to water and corroborate the hydrolytic stability of the Y-shp-MOF-5. Hence, the shape of the water vapor isotherm only reflected the water adsorption in distinct energetic sites. First at low pressure, water molecules were primarily adsorbed on the exposed open metal sites. The initial 5 wt % water uptake, as depicted, shown in FIG. 24 (black circles), is equivalent to the adsorption of eight water molecules and can be attributed to the water molecules coordinated to the unsaturated Y sites in the cluster and hydrogen bonded with the hydroxyl groups on the cluster. The saturation of all open metal sites occurred at a 10% RH followed by a steady uptake (at ≈5 wt %) up to 50% RH. The insignificant water uptake below 50% RH indicated the low affinity of water to the Y-shp-MOF-5 surface due plausibly to the hydrophobicity of the organic ligand; suggesting the necessity of a higher driving force for additional water adsorption, i.e., a relatively higher water vapor pressure promoted further adsorption of water molecules into the available channels, consequently reaching full saturation at 70% RH with a 50 wt % uptake.

The characteristic s-shape isotherm and the occurrence of a wide hysteresis-like loop were highly unusual for microporous materials; it was more common in mesoporous materials, where the hysteresis reflects the irreversibility of capillary condensation. Nonetheless, the unique behavior of water adsorption for the Y-shp-MOF-5 may be explained by the open metal sites of Y-shp-MOF-5 and the exposed hydroxyl groups in the cluster, which acted as primary adsorption sites, via coordination or hydrogen bonding, due to their high affinity for water molecules and accounted for the initial adsorption of water molecules (5 wt %-6 wt %) at very low % RH (<10% RH). After the first water adsorption step, the material practically did not adsorb any additional water until 50% RH. As the pressure increased, water clusters started growing until these clusters built enough dispersive energy to sustain it inside the pores. This was plausibly occurring at 50% RH for the Y-shp-MOF-5, manifested by the steep uptake where energetically favorable water clusters formed on secondary sites via hydrogen bonding between water molecules, ultimately leading to instant pore filling as the clusters connected across the pore system to form superclusters. On the other hand, as observed in FIG. 24, at 25° C. and below 75%, the desorption branch curve was not superimposing with the adsorption branch (goes over the adsorption curve), due to the presence of the aforementioned superclusters in the pores. In fact, in order for the water molecules to escape from the pores, a driving force was needed (i.e. reducing RH to 45% for Y-shp-MOF-5) to dissociate the superclusters into smaller clusters (having weaker dispersive forces); hence promoting the progressive desorption of the water molecules from the pores while the coordinated water molecules to the open metal sites remain adsorbed.

A new hydrolytically stable microporous RE-based MOF with a rare shp topology was synthesized. The resultant Y-shp-MOF-5 exhibited distinctive water vapor adsorption properties in contrast to other microporous MOF materials. The combination of the steep adsorption instigated at around 55% RH-60% RH, associated with the growth of water clusters, and the shifted desorption to 45% RH made the Y-shp-MOF-5 a strong contender for humidity-triggered water capture-and-release systems for adsorption-based moisture-controlled processes. The Y-shp-MOF-5 maintained its structural integrity and distinctive performance over more than 1000 moisture adsorption-desorption cycles in the ideal range of application with a water vapor working uptake between 35 wt %-40 wt %. These unique features of high durability and robustness, gave the Y-shp-MOF-5 a clear-cut advantage over other water vapor adsorbents in general, and MOFs in particular, for moisture control in confined spaces, such as aircrafts and submarines. Most importantly, the Y-shp-MOF-5 can adsorb and desorb large amounts of water just by adjusting the relative humidity (water vapor pressure) at ambient temperature and can be implemented in energy-efficient autonomous moisture control systems. Based on these findings, further work is in progress to investigate the applicability of the Y-shp-MOF-5 in combined adsorption desalination and adsorption-based heat pump applications.

Metal-organic frameworks operating in water vapor-related applications were studied. In particular, in situ SCXRD were studied to explore a unique mechanism of water sorption on a novel highly connected Rare-Earth (RE)-based shp-MOF. As provided herein, Y-shp-MOF-5 was capable of uniquely adsorbing and desorbing water within the recommended relative humidity range (45% RH to 65% RH) set by the occupational health and safety, aerospace and aviation agencies standards. Y-shp-MOF-5 exhibited exceptional structural integrity, robustness and humidity-control performance as inferred from the unprecedentedly large number (thousand) of water vapor adsorption-desorption cycles. The resultant working water uptake of 35 wt % was regulated solely by a simple adjustment of the relative humidity, positioning this hydrolytically stable MOF as a unique prospective adsorbent for indoor humidity control such as space shuttles, aircraft cabins and air-conditioned buildings. Y-shp-MOF is a highly connected MOF that displayed a unique energy-efficient dual humidifying/dehumidifying functionality in the optimal range of about 45% to 65% relative humidity, with an uptake at the thermodynamic equilibrium of about 0.5 g/g. The observed s-shape of the water adsorption isotherm, where the main loading and discharge occurring at the aforementioned ranges was within ASHREA recommendations in order to maintain a comfortable environment within enclosed spaces, was particularly beneficial in an autonomous moisture controlled swing adsorption technology (MSA).

TABLE 1

Crystal data and structure refinement for 1.

| | |
|---|---|
| Identification code | 1 (as synthesized) |
| Empirical formula | $C_{108}H_{106}N_3O_{47}Y_9$ |
| Formula weight | 2998.14 |
| Crystal system, space group | Hexagonal, $P6_3/mmc$ |
| Unit cell dimensions | a = 22.995(2) Å, c = 24.684(2) Å |
| Volume | 10342(2) Å$^3$ |
| Z, calculated density | 2, 0.963 g cm$^{-3}$ |
| F(000) | 3004 |
| Temperature (K.) | 100.0(1) |
| Radiation type | Cu Kα |
| Absorption coefficient | 3.66 mm$^{-1}$ |
| Absorption correction | Multi-scan |
| Max and min transmission | 1.000 and 0.862 |
| Crystal size | 0.02 × 0.03 × 0.03 mm |
| Shape, color | Hexagonal bipyramid, colorless |
| θ range for data collection | 2.9-67.5° |
| Limiting indices | $-25 \leq h \leq 25, -24 \leq k \leq 26,$ $-29 \leq l \leq 28$ |
| Reflection collected/unique/ observed with I > 2σ(I) | 72757/3416 ($R_{int}$ = 0.050)/3016 |
| Completeness to $θ_{max}$ = 67.5° | 98.5% |
| Refinement method | Full-matrix least-squares on F$^2$ |
| Data/restraints/parameters | 3416/44/157 |
| Final R indices [I > 2σ(I)] | $R_1$ = 0.074, $wR_2$ = 0.217 |
| Final R indices (all data) | $R_1$ = 0.079, $wR_2$ = 0.227 |
| Weighting scheme | $[σ^2(F_o^2) + (0.1741P)^2 + 5.1421P]^{-1}$* |
| Goodness-of-fit | 1.07 |
| Largest cliff peak and hole | 1.11 and −1.44 e Å$^{-3}$ |

*P = $(F_o^2 + 2F_c^2)/3$

TABLE 2

Crystal data and structure refinement for 2.

| | |
|---|---|
| Identification code | 2 (0% RH) |
| Empirical formula | $C_{108}H_{106}N_3O_{47}Y_9$ |
| Formula weight | 2944.09 |
| Crystal system, space group | Hexagonal, $P6_3/mmc$ |
| Unit cell dimensions | a = 22.1503(5) Å, c =24.4010(7) Å |
| Volume | 10368.1(6) Å$^3$ |
| Z, calculated density | 2, 0.943 g cm$^{-3}$ |
| F(000) | 2944 |
| Temperature (K.) | 296.0(1) |
| Radiation type | Cu Kα |
| Absorption coefficient | 3.63 mm$^{-1}$ |
| Absorption correction | Multi-scan |
| Max and min transmission | 1.000 and 0.816 |
| Crystal size | 0.02 × 0.03 × 0.03 mm |
| Shape, color | Hexagonal bipyramid, colorless |
| θ range for data collection | 4.0-67.5° |
| Limiting indices | $-25 \leq h \leq 24, -26 \leq k \leq 16,$ $-28 \leq l \leq 28$ |
| Reflection collected/unique/ observed with I > 2σ(I) | 75389/3432 ($R_{int}$ = 0.055)/2951 |
| Completeness to $θ_{max}$ = 67.5° | 98.8% |
| Refinement method | Full-matrix least-squares on F$^2$ |
| Data/restraints/parameters | 3432/42/152 |
| Final R indices [I > 2σ(I)] | $R_1$ = 0.055, $wR_2$ = 0.154 |
| Final R indices (all data) | $R_1$ = 0.063, $wR_2$ = 0.176 |
| Weighting scheme | $[σ^2(F_o^2) + (0.0959P)^2 + 6.2463P]^{-1}$* |
| Goodness-of-fit | 1.12 |
| Largest cliff peak and hole | 1.15 and −0.55 e Å$^{-3}$ |

*P = $(F_o^2 + 2F_c^2)/3$

TABLE 3

Crystal data and structure refinement for 3.

| | |
|---|---|
| Identification code | 3 (22% RH) |
| Empirical formula | $C_{108}H_{106}N_3O_{47}Y_9$ |
| Formula weight | 2998.14 |
| Crystal system, space group | Hexagonal, $P6_3/mmc$ |
| Unit cell dimensions | a = 21.996(2) Å, c = 24.912(2) Å |
| Volume | 10438(2) Å$^3$ |
| Z, calculated density | 2, 0.954 g cm$^{-3}$ |
| F(000) | 3004 |
| Temperature (K.) | 296.0(1) |
| Radiation type | Mo Kα |
| Absorption coefficient | 2.52 mm$^{-1}$ |
| Absorption correction | Multi-scan |
| Max and min transmission | 1.000 and 0.726 |
| Crystal size | 0.02 × 0.03 × 0.03 mm |
| Shape, color | Hexagonal bipyramid, colorless |
| θ range for data collection | 2.7-23.3° |
| Limiting indices | −24 ≤ h ≤ 22, −20 ≤ k ≤ 24, −21 ≤ l ≤ 27 |
| Reflection collected/unique/ observed with I > 2σ(I) | 48234/2795 ($R_{int}$ = 0.175)/1705 |
| Completeness to $θ_{max}$ = 21.3° | 99.4% |
| Refinement method | Full-matrix least-squares on F$^2$ |
| Data/restraints/parameters | 2795/52/133 |
| Final R indices [I > 2σ(I)] | $R_1$ = 0.075, $wR_2$ = 0.221 |
| Final R indices (all data) | $R_1$ = 0.133, $wR_2$ = 0.248 |
| Weighting scheme | $[σ^2(F_o^2) + (0.1955P)^2]^{-1}$* |
| Goodness-of-fit | 1.03 |
| Largest cliff peak and hole | 0.96 and −0.74 e Å$^{-3}$ |

*P = $(F_o^2 + 2F_c^2)/3$

TABLE 4

Crystal data and structure refinement for 4.

| | |
|---|---|
| Identification code | 4 (100% RH) |
| Empirical formula | $C_{108}H_{106}N_3O_{47}Y_9$ |
| Formula weight | 2998.14 |
| Crystal system, space group | Hexagonal, $P6_3/mmc$ |
| Unit cell dimensions | a = 22.097(1) Å, c = 24.705(2) Å |
| Volume | 10447(2) Å$^3$ |
| Z, calculated density | 2, 0.953 g cm$^{-3}$ |
| F(000) | 3004 |
| Temperature (K.) | 296.0(1) |
| Radiation type | Cu Kα |
| Absorption coefficient | 2.52 mm$^{-1}$ |
| Absorption correction | Multi-scan |
| Max and min transmission | 0.043 and 0.017 |
| Crystal size | 0.02 × 0.03 × 0.03 mm |
| Shape, color | Hexagonal bipyramid, colorless |
| θ range for data collection | 1.4-23.0° |
| Limiting indices | −24 ≤ h ≤ 24, −24 ≤ k ≤ 24, −27 ≤ l ≤ 13 |
| Reflection collected/unique/ observed with I > 2σ(I) | 38668/2720 ($R_{int}$ = 0.120)/1758 |
| Completeness to $θ_{max}$ = 24.7° | 99.7% |
| Refinement method | Full-matrix least-squares on F$^2$ |
| Data/restraints/parameters | 2720/32/135 |
| Final R indices [I > 2σ(I)] | $R_1$ = 0.089, $wR_2$ = 0.261 |
| Final R indices (all data) | $R_1$ = 0.130, $wR_2$ = 0.302 |
| Weighting scheme | $[σ^2(F_o^2) + (0.1803P)^2]^{-1}$* |
| Goodness-of-fit | 1.12 |
| Largest cliff peak and hole | 1.32 and −1.11 e Å$^{-3}$ |

*P = $(F_o^2 + 2F_c^2)/3$

What is claimed is:

1. A method of moisture control in an environment, comprising:
    adsorbing and/or desorbing water vapor in an environment having a relative humidity by exposing a metal-organic framework (MOF) to the relative humidity of the environment, the MOF including one or more of a rare earth metal ion component and one or more of a tetratopic ligand component, wherein a topology of the MOF is a square and hexagonal-prism (shp).

2. The method of claim 1, wherein the MOF adsorbs water vapor above a first relative humidity and desorbs water vapor below a second relative humidity.

3. The method of claim 2, wherein the first relative humidity is different from the second relative humidity.

4. The method of claim 2, wherein the first relative humidity is 60% and the second relative humidity is 40%.

5. The method of claim 1, wherein the environment has a relative humidity within the range of 50-85% and the method comprises absorbing an amount of water vapor sufficient to reduce the relative humidity in the environment to about 40%.

6. The method of claim 1, further comprising:
    sensing the relative humidity in the environment; and
    adsorbing water vapor on the MOF if the relative humidity is above a first level, sufficient to control moisture in the environment.

7. The method of claim 6, further comprising desorbing water vapor from the MOF if the relative humidity is below a second level.

8. The method of claim 1, wherein the environment is a confined space without any circulation of air.

9. The method of claim 1, further comprising hydrating the MOF by soaking the MOF in water before the exposing step.

10. The method of claim 1, further comprising activating the MOF by exposing the MOF to an activation temperature before the exposing step.

11. The method of claim 1, wherein the rare earth metal ion component is a nonanuclear cluster of rare earth metal ions.

* * * * *